(12) United States Patent
Shin et al.

(10) Patent No.: US 10,823,694 B2
(45) Date of Patent: Nov. 3, 2020

(54) SYSTEM AND METHOD FOR SINGLE-STEP ELISA VIA LOCAL PH MODULATION

(71) Applicant: Robert Bosch GmbH, Stuttgart (DE)

(72) Inventors: Young Shik Shin, Mountain View, CA (US); Nadezda Fomina, Redwood City, CA (US); Christopher Johnson, Mountain View, CA (US); Christoph Lang, Sunnyvale, CA (US); Patrick Staley, Sunnyvale, CA (US)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 16/032,144

(22) Filed: Jul. 11, 2018

(65) Prior Publication Data
US 2019/0017954 A1 Jan. 17, 2019

Related U.S. Application Data

(60) Provisional application No. 62/531,836, filed on Jul. 12, 2017.

(51) Int. Cl.
*G01N 27/327* (2006.01)
*G01N 27/30* (2006.01)
(Continued)

(52) U.S. Cl.
CPC ....... *G01N 27/3275* (2013.01); *G01N 27/302* (2013.01); *G01N 33/533* (2013.01);
(Continued)

(58) Field of Classification Search
CPC ............. G01N 27/3275; G01N 27/302; G01N 27/3272; G01N 33/84; G01N 33/5375;
(Continued)

(56) References Cited

U.S. PATENT DOCUMENTS 5,091,318 A * 2/1992 Anawis .................. A61K 39/35
436/513
5,334,537 A 8/1994 Lee et al.
(Continued)

FOREIGN PATENT DOCUMENTS

WO 2017003126 A1 1/2017

OTHER PUBLICATIONS

International Search Report and Written Opinion corresponding to International Patent Application No. PCT/US2018/041591 (12 pages).

*Primary Examiner* — Melanie Brown
(74) *Attorney, Agent, or Firm* — Maginot, Moore & Beck LLP

(57) ABSTRACT

A method for detecting a presence and/or a concentration of a target substance in a reagent solution using enzyme-linked immunosorbent assay (ELISA) includes binding the target substance directly or indirectly to an electrode, and binding a detection agent directly or indirectly to the bound target substance. The method further includes modulating a pH of only a portion of the reagent solution in which the bound target substance and the bound detection agent are located using the electrode, the modulated pH of the portion of the reagent solution causing the bound detection agent to undergo a change, and detecting the change in the bound detection agent. The detected change corresponds to the presence of the target substance in the reagent solution and/or the concentration of the target substance in the reagent solution.

11 Claims, 19 Drawing Sheets

(51) Int. Cl.
*G01N 33/53* (2006.01)
*G01N 33/533* (2006.01)
*G01N 33/84* (2006.01)
*G01N 33/537* (2006.01)
*G01N 33/543* (2006.01)

(52) U.S. Cl.
CPC ..... *G01N 33/5306* (2013.01); *G01N 33/5375* (2013.01); *G01N 33/5438* (2013.01); *G01N 33/54386* (2013.01); *G01N 33/84* (2013.01); *G01N 27/3272* (2013.01); *G01N 33/5304* (2013.01); *G01N 33/54306* (2013.01)

(58) Field of Classification Search
CPC ......... G01N 33/54386; G01N 33/5438; G01N 33/5306; G01N 33/533; G01N 33/54306; G01N 33/5304
See application file for complete search history.

(56) References Cited

U.S. PATENT DOCUMENTS

| | | | |
|---|---|---|---|
| 5,387,527 A * | 2/1995 | Sternberg | G01N 33/542 |
| | | | 436/172 |
| 2011/0278258 A1 | 11/2011 | Kavusi et al. | |
| 2014/0274760 A1 | 9/2014 | Fomina et al. | |
| 2016/0003763 A1* | 1/2016 | Johnson | G01N 27/226 |
| | | | 205/777.5 |
| 2017/0010238 A1 | 1/2017 | Johnson et al. | |
| 2018/0188156 A1* | 7/2018 | Peumans | G01N 21/648 |

* cited by examiner

| FRET | | Fluorophore name | Excitation (nm) | Emission (nm) | pH sensitive? |
|---|---|---|---|---|---|
| Example pair #1 | Donor | FITC | 490 | 525 | Yes (active in neutral-basic condition) |
| | Acceptor | TRITC | 557 | 576 | No |
| Example pair #2 (probably redundant of the pair #1) | Donor | FAM | 492 | 518 | Yes (active in neutral-basic condition) |
| | Acceptor | TRITC | 557 | 576 | No |
| Example pair #3 | Donor | Oregon Green 488 | 496 | 524 | Yes (active in neutral-basic condition) |
| | Acceptor | TMR | 542 | 574 | No |

FIG. 16

SYSTEM AND METHOD FOR SINGLE-STEP ELISA VIA LOCAL PH MODULATION

This application claims the benefit of priority of U.S. provisional application Ser. No. 62/531,836, filed on Jul. 12, 2017, the disclosure of which is herein incorporated by reference in its entirety.

BACKGROUND

Enzyme-linked immunosorbent assay ("ELISA") is a protein detection method for various applications ranging from fundamental biological studies to disease diagnostics. ELISA is widely used in academic research labs, medical test reference labs, and hospitals to detect target substances from various types of biological specimens. The ELISA process is based upon the principle that a target substance is identified by a primary/capture agent. The presence of the target substance is visualized through a detection/secondary antibody onto which there is bound an enzyme or a fluorescent dye. A signal intensity from an enzymatic reaction product of the enzyme or from the fluorescent dye is measured as the output of the assay.

Some point-of-care systems utilize ELISA for target substance detection, and ELISA is a commonly used test format for diagnosing diseases. ELISA, however, has not been standardized for most cases and even commercial ELISA kits are often unreliable. Test result variation among different labs is another major concern for the practical application of ELISA in disease diagnostics. The known ELISA process has multiple reaction steps, each having a thorough washing step. Having multiple reaction steps and washing steps in an ELISA protocol increases the chance of introducing errors, and it is critical to avoid the introduction of errors for medical diagnostic tests or multiparameter screening type of assays. Multiple washing steps, for example, causes imprecision because non-complete washing induces false positive signals and/or noise, while overly aggressive washing lowers the signal intensity by dissociating antibody bound target substances.

The multiple reaction steps also make it more difficult and complicated to develop a portable ELISA-based system. Common features of portable ELISA-based systems include a disposable microfluidics cartridge, mechanical components for reagent solution flow control, and optical detection components. Mechanical components such as pumps, motors, and syringes typically require a large physical space, a complex software control algorithm, and a high level of potential maintenance.

Accordingly, known ELISA processes and ELISA-based systems have multiple reaction and washing steps, which increase the chance of technician-driven errors, the quantities of reagent solutions necessary, and the variability from test to test. Having multiple steps of reagent solution handling is a major barrier for instrument automation and miniaturization as well, especially for a point-of-care system. As a result, further developments in the areas of ELISA processes and ELISA-based systems are desired.

SUMMARY

According to an exemplary embodiment of the disclosure, a method for detecting a presence and/or a concentration of a target substance in a reagent solution using enzyme-linked immunosorbent assay (ELISA) includes binding the target substance directly or indirectly to an electrode, and binding a detection agent directly or indirectly to the bound target substance. The method further includes modulating a pH of only a portion of the reagent solution in which the bound target substance and the bound detection agent are located using the electrode, the modulated pH of the portion of the reagent solution causing the bound detection agent to undergo a change. The method also includes detecting the change in the bound detection agent. The detected change corresponds to the presence of the target substance in the reagent solution and/or the concentration of the target substance in the reagent solution.

According to another exemplary embodiment of the disclosure, a method for detecting a target substance using enzyme-linked immunosorbent assay (ELISA) includes binding the target substance directly or indirectly to a first electrode located in a test well including a reagent solution, and adding a detection agent to the test well. A bound portion of the detection agent is bound directly or indirectly to the bound target substance and an unbound portion of the detection agent is unbound to the bound target substance. The method further includes adding additional detection agent to a control well that includes additional reagent solution and that does not include the target substance. A second electrode is located in the control well. The method includes modulating a pH of only a portion of the reagent solution in the test well in which the bound target substance is located to cause the bound portion of the detection agent located in the portion of the reagent solution and the unbound portion of the detection agent located in the portion of the reagent solution to undergo a first change using the first electrode, and modulating a pH of only a corresponding portion of the additional reagent solution located in the control well to cause a corresponding portion of the additional detection agent located in the corresponding portion of the additional reagent solution to undergo a second change using the second electrode. The method further includes detecting the first change as a first detected value, detecting the second change as a second detected value, and generating a test value as a comparison of the first detected value to the second detected value. The generated test value corresponds to a presence of the target substance in the test well and/or a concentration of the target substance in the test well.

According to yet another exemplary embodiment of the disclosure, a system for detecting a presence and/or a concentration of a target substance using enzyme-linked immunosorbent assay (ELISA) includes a test well, a reagent solution located in the test well and including the target substance, and at least one electrode located in the test well in direct contact with the reagent solution. The target substance binds directly or indirectly to the at least one electrode. The system further includes a detection agent including a pH-sensitive reporter, the detection agent configured to bind directly or indirectly to the bound target substance, and a controller electrically connected to the at least one electrode. The controller is configured to modulate a pH of only a portion of the reagent solution in which the bound target substance and the bound detection agent are located using the electrode. The modulated pH of the portion of the reagent solution causes the pH-sensitive reporter of the bound detection agent to undergo a change. The controller detects the change in the pH-sensitive reporter, and the detected change corresponds to the presence of the target substance in the reagent solution and/or the concentration of the target substance in the reagent solution.

According to a further embodiment, a system for detecting a presence and/or a concentration of a target substance using enzyme-linked immunosorbent assay (ELISA)

includes a test well, a reagent solution located in the test well and including the target substance, at least one electrode located in the test well in direct contact with the reagent solution, a capture agent including one of a pH-sensitive donor molecule and an acceptor molecule, the capture agent bound to the at least one electrode, the target substance binding directly or indirectly to the capture agent, a detection agent including the other of the pH-sensitive donor molecule and the acceptor molecule, the detection agent configured to bind directly or indirectly to the bound target substance, and a controller electrically connected to the at least one electrode and configured to modulate a pH of only a portion of the reagent solution in which the bound detection agent is located using the electrode, the modulated pH of the portion of the reagent solution causing the pH-sensitive donor molecule to undergo a first change, and the first change causing the acceptor molecule to undergo a second change, and detect the second change in the acceptor molecule, the detected second change corresponding to the presence of the target substance in the reagent solution and/or the concentration of the target substance in the reagent solution.

BRIEF DESCRIPTION OF THE FIGURES

FIG. 16 is a chart illustrating exemplary donor and acceptor pairs for use in the FRET-based system of FIG. 14A;

DETAILED DESCRIPTION

Figure 1:
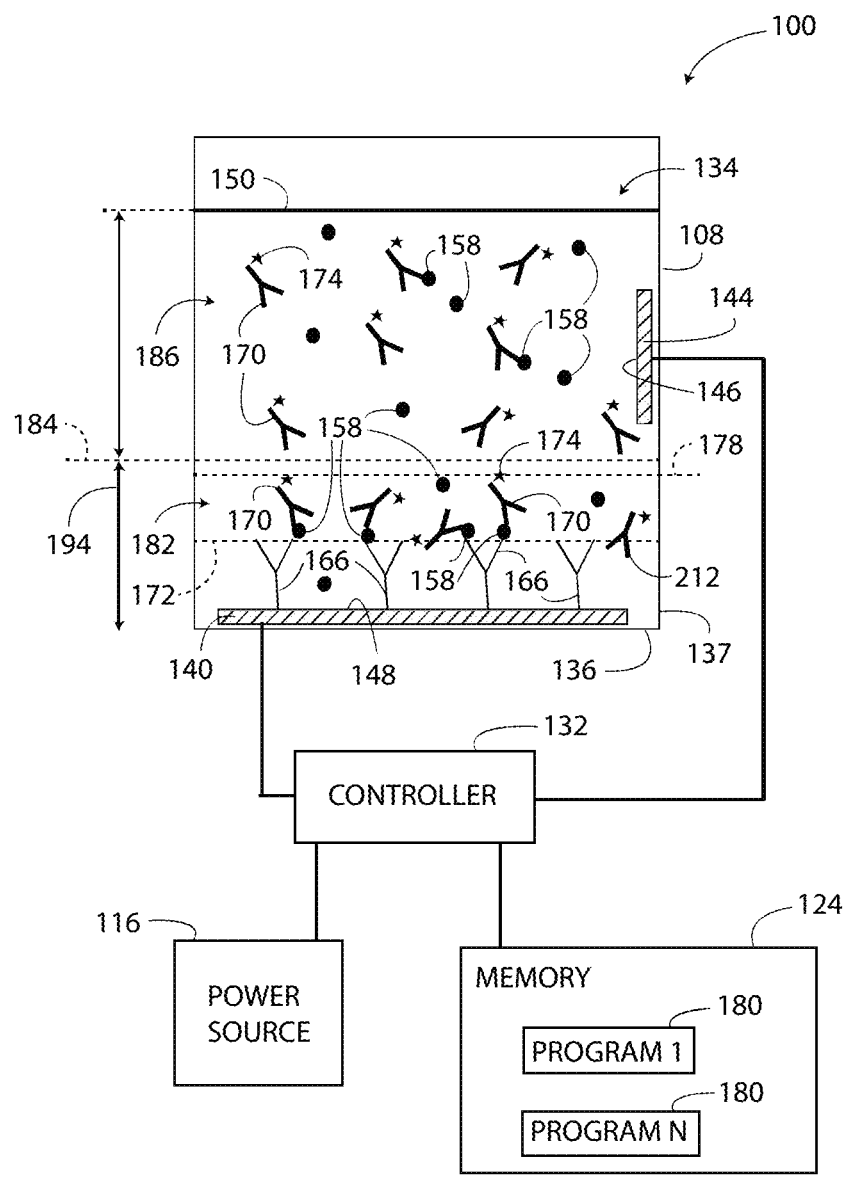
FIG. 1 is a block diagram illustrating a single-step ELISA system including a well, a controller, a power source, and a memory, the ELISA system, in one embodiment, uses a localized change in pH of a reagent solution to detect the presence of and/or the concentration of a target substance in a test sample.

For the purpose of promoting an understanding of the principles of the disclosure, reference will now be made to the embodiments illustrated in the drawings and described in the following written specification. It is understood that no limitation to the scope of the disclosure is thereby intended. It is further understood that this disclosure includes any alterations and modifications to the illustrated embodiments and includes further applications of the principles of the disclosure as would normally occur to one skilled in the art to which this disclosure pertains.

For the purposes of the disclosure, the phrase "A and/or B" means (A), (B), or (A and B). For the purposes of the disclosure, the phrase "A, B, and/or C" means (A), (B), (C); (A and B); (A and C); (B and C); or (A, B and C).

The terms "comprising," "including," "having," and the like, as used with respect to the embodiments of the disclosure, are synonymous.

The disclosure describes a system and a method for performing ELISA with a single mixture of reagent solutions in a single reaction step. As used herein, a "single-step ELISA" refers to a system and/or a method that includes only one reaction step to configure the system for the detection of a target substance. The single-step ELISA may include one or more washing steps.

The systems and methods disclosed herein utilize electrochemical pH modulation or an ionic concentration gradient in a defined region combined with pH-sensitive reporter systems such as pH-sensitive fluorescent dyes or pH-sensitive enzyme reactions. In one embodiment, the disclosed ELISA system generates test results without requiring the user to change solutions and without electronic test readout equipment. Moreover, the ELISA systems disclosed herein have only one washing step. Accordingly, the ELISA systems disclosed herein are simple and compact, and also have enhanced test accuracy and reproducibility.

As shown in FIG. 1, a biosensor provided as a single-step ELISA system 100 includes a sample well 108, a power source 116, a memory 124, and a controller 132. The well 108 is typically formed on a glass slide (or any other type of slide), a semiconductor, or a plastic substrate. Additionally or alternatively, the well 108 may be one of many substantially identical wells 108 formed in a microtiter plate (not illustrated). Only one well 108 of the potentially many wells 108 is shown in FIG. 1. The exemplary well 108 defines an open cylindrical volume for holding a liquid mixture referred to generally as a sample 134. The well 108, in one embodiment, holds approximately 0.5 nl to 5 ml of the sample 134. In another embodiment, the well 108 is a closed chamber connected to microfluidic channels (not shown).

The well 108 includes a bottom surface 136 and a side surface 137 extending from the bottom surface 136. A first electrode 140 and a second electrode 144 are located in the well 108. The electrode 140, which is also referred to herein as the bottom electrode, is located on, at, or near the bottom surface 136 of the well 108 within the cylindrical volume defined by the well 108. At least a portion of the electrode 140 is positioned to contact directly the sample 134 contained by the well 108. In the illustrated embodiment, an upper surface 148 (i.e. the surface of the electrode 140 facing away from the bottom surface 136 of the well 108) of the electrode 140 is positioned to contact directly the sample 134. In one embodiment, the electrode 140 is substantially flat and has a circular periphery that substantially corresponds to the bottom surface 136 of the well 108. In other embodiments, the electrode 140 has any suitable shape. The upper surface 148, in one embodiment, is patterned, shaped, or otherwise configured, such that the sample 134 has a desired electrochemical response to the electrode 140 being energized. In particular, the upper surface 148 of the electrode 140, in one embodiment, is patterned to cause a reagent solution 150 of the sample 134 to resist buffering effects during pH modulation. Although, FIG. 1 illustrates the system 100 as including only one of the electrodes 140, the system 100, in other embodiments, includes any suitable number of the electrodes 140 as appropriate for the area and the shape of the well 108. For example, in one embodiment, the system 100 includes more than ten of the electrodes 140, which are spaced apart from each other on the bottom surface 136 of the well 108.

The electrode 144, which is also referred to herein as a side electrode, is mounted on, at, or near the side surface 137 of the well 108. The electrode 144 is positioned to at least partially contact directly the sample 134 contained by the well 108. The electrode 144 is spaced apart from the electrode 140 and does not contact directly the electrode 140. As shown in FIG. 1, in one embodiment, the electrode 144 defines a main surface 146 that is substantially perpendicular to the upper surface of the electrode 140. In other embodiments, the electrode 144 has any suitable shape including cylindrical and planar. Moreover, in some embodiments the electrode 144 has a "mesh-like" or perforated configuration in which the electrode 144 includes a plurality of holes therethrough. The electrode 144, in other embodiments, is not perpendicular to the electrode 140 and may have any suitable angular orientation with respect to the electrode 140. Moreover, in other embodiments, the electrode 144 is positioned anywhere in the well 108 that configures the electrode 144 for contact with the sample 134. For example, the electrode 144 and the electrode 140 may be located on the same surface. Additionally or alternatively, the electrode 144 may be immersed in the middle of the sample 134, such that the electrode contacts the sample 134 and is spaced apart from the surfaces of the well 108. For example, the electrode 144 may be connected to the end of a probe (not shown) that is insertable into the sample 134.

The electrodes 140, 144 are formed from any suitable material(s) including, but not limited to, metals, such as platinum, gold, and silver; metal oxides, such as indium tin oxide and fluorine doped tin oxide; and carbon materials, such as glassy carbon or graphite. The electrodes 140, 144 need not be formed from the same material(s). For example, the bottom electrode 140 may be formed from a first material and the side electrode 144 may be formed from a second material that is different from the first material.

As shown in FIG. 1, the sample 134 contained by the well 108 includes the reagent solution 150, a target substance 158, and a detection agent 170. A capture agent 166 is also included in the well 108, but is typically not considered as part of the sample 134. The reagent solution 150, in one embodiment, is an aqueous solution that exhibits a localized change in pH in response to an electrical stimulus. The reagent solution 150 includes electroactive molecules capable of electrochemical oxidation and/or electrochemical reduction, which results in generation or consumption of protons to modulate the pH of at least a portion of the reagent solution 150 in response to an electrical signal coupled to at least one of the electrodes 140, 144. The reagent solution 150 may include electrochemically active agents, buffer inhibitors, buffer solutions, enzymes, enzyme substrates, electrolytes, or any combination thereof to result in the localized change in pH. At least a portion of the electrodes 140, 144 are in direct contact with the reagent solution 150. In a specific embodiment, the reagent solution 150 includes electrolytes, such as sodium sulfate, sodium or potassium chloride, sodium or potassium bromide, sodium or potassium iodide, sodium or potassium perchlorate, sodium or potassium nitrate, tetraalkylammonium bromide and tetraalkylammonium iodide. Exemplary buffer inhibitors of the reagent solution 150 include, but are not limited to, poly(allylamine hydrochloride), poly(diallyl dimethyl ammonium chloride), poly(vinylpyrrolidone), poly(ethyleneimine), poly(vinylamine), poly(4-vinylpyridine), and tris (2-carboxyethyl) phosphine hydrochloride. In some embodiments, the reagent solution 150 includes a water-miscible organic co-solvent selected from the group consisting of acetonitrile, dimethyl sulfoxide (DMSO), dimethyl formamide (DMF), N,N-dimethyl acetamide (DMAc), and mixtures thereof. The organic co-solvent, if included, promotes pH modulation of the reagent solution 150 according to a method 300 (FIG. 3) described herein. The reagent solution 150 may also be referred to herein as simply a "reagent."

In another embodiment, the reagent solution 150 is configured for reversible electrochemical oxidation/reduction of quinone derivatives, hydrazine derivatives, or water in order to induce a rapid change in pH in a localized region. The pH in the localized region can be modulated with the quinone derivative in the range of 0 to 10. The pH modulation limit to the basic end depends on the pKa of the specific quinone derivative but there is no theoretical limit to the acidic end. In such an embodiment, the reagent solution 150 is provided as any quinone derivative, hydrazine derivative, or phenol-Ru $(2,2'\text{-bipyridine})_3^{2+}$, or any other molecule and/or compound that undergoes proton coupled electron transfer.

The target substance 158 includes any bio-molecule including, but not limited to, proteins, peptides, antibodies, nucleic acids, extracellular vesicles, hormones, and antigens. Exemplary sources of target substances 158 include body fluids from humans and animals such as blood, serum, saliva, urine, sweat; biological cells; or tissue samples. Accordingly, the system 100 is suitable for both medical and veterinary applications. Additionally or alternatively, the target substance 158 includes consumables such as milk, wine, fruit, vegetables, baby food, or water. The target substance 158 is directly or indirectly bound to the electrode 140, as described herein.

With continued reference to FIG. 1, the capture agent 166 is attached/bound to the upper surface 148 of the electrode 140. The capture agent 166 is any molecule and/or compound that immobilizes the target substance 158, as shown by the four exemplary molecules of immobilized target substance 158 in FIG. 1. For example, the capture agent 166 may be a substance to which the target substance 158 adsorbs in order to immobilize the target substance 158.

Exemplary, capture agents 166 include, but are not limited to, antibodies, peptides, nucleic acids, small molecules, and/or any other suitable molecules. In one embodiment, the capture agent 166 is located only on the upper surface 148 of the bottom electrode 140 and is not located on any other surface within the well 108. In such an embodiment, the upper surface 148 is an occupied area and the other areas and regions of the well 108 are unoccupied areas from which the capture agent 166 has been blocked. Specifically, the capture agent 166 is blocked from an unoccupied area including the side surface 137 of the well 108 and the side electrode 144. Moreover, the capture agent 166 is applied or formed on the electrode 140 in a manner that the molecules of the capture agent 166 define an average upper level 172 (FIG. 1) above which none (or substantially none) of the capture agent 166 contributes to the signal. That is, all (or substantially all) of the molecules of the capture agent 166 are located below the upper level 172 of the capture agent 166. In other embodiments, the capture agent 166 is located on any other surface of the well 108, the electrode 140, and/or the electrode 144; however, only the capture agent 166 located below a modulation line 184 (FIG. 1, see discussion set forth below) contributes to the output of the detection agent 170.

The molecules of the capture agent 166 are attached to the electrode 140 using any desired process. For example, processes including linker molecule-based chemistry, electrostatic adsorption, and physical adsorption are typically used to attach or to link the capture agent 166 to the electrode 140. In some embodiments, surface treatment is applied to the bottom surface 136 of the well 108 and/or the bottom electrode 140 to enable the capture agent 166 to bind even more effectively to the electrode 140.

In the figures, the capture agent 166 is shown at a much larger scale than the electrodes 140, 144 to aid in understanding, describing, and illustrating the system 100. Since the capture agent 166 is bound to the electrode 140, the capture agent 166 is not free flowing within the reagent solution 150 as are the target substance 158 and the detection agent 170. Moreover, in one embodiment, the capture agent 166 is added to the well 108 prior to adding the sample 134. The target substance 158 is directly or indirectly bound to the capture agent 166 depending on the type of ELISA utilized (see discussion of FIG. 10, herein).

The detection agent 170 is any molecule and/or compound that forms a complex with the target substance 158. Forming a "complex" includes absorbing, linking, and/or otherwise binding to the target substance 158. For example, the detection agent 170 may be provided as antibodies, peptides, nucleic acids, small molecules, and/or any other suitable molecule. As shown in FIG. 1, when the detection agent 170 is in the presence of the target substance 158, the detection agent 170 binds to (or forms a complex with) the target substance 158. Some of the detection agent 170 binds to instances of the target substance 158 that have been immobilized by the capture agent 166, thereby forming a chain (or sandwich) of molecules including the capture agent 166, the target substance 158, and the detection agent 170 that are bound to the electrode 140. The chain of molecules defines an average height or a maximum height as identified by the immobilized height line 178 shown in FIG. 1. The immobilized height line 178 is determined, in one embodiment, based on a sum total of the longest dimension of each of the molecules 158, 166, 170. All or substantially all of the detection agent 170 molecules that are bound to an immobilized target substance 158 are located below the immobilized height line 178.

As shown in FIG. 1, the detection agent 170 includes a tag 174. The tag 174 is a detection enzyme or other molecule that has a pH-dependent property or characteristic. For example, in one embodiment, the tag 174 is a pH-sensitive reporter such as a pH-sensitive fluorescent dye that exhibits light emission when in solution with a reagent solution 150 having a first pH and does not exhibit light emission when in solution with a reagent solution 150 having a second pH that is different from the first pH. For example, the tag 174 emits substantially no light when the reagent solution 150 has a pH of 7.0 and emits a human perceptible and machine detectable intensity of light when the reagent solution 150 has a pH of 4.5. Exemplary tags 174 include at least Oregon Green, FAM (e.g. 6-FAM (6-Carboxyfluorescein)), LysoSensor Green, pHrodo Green, Protonex dyes (as exemplary dyes for acidic conditions), HEX (hexachlorofluorescein), JOE (NHS Ester, 6-carboxy-4',5'-dichloro-2',7'-dimethoxyfluorescein), TET (tetrachlorofluorescein), and horseradish peroxidase enzyme (HRP), among others. Moreover other exemplary tags 174 include fluorescent proteins such as GFP (green fluorescent protein), YFP (yellow fluorescent protein), CFP (cyan fluorescent protein), and their derivatives (as exemplary dyes for neutral-basic conditions).

Figure 2:
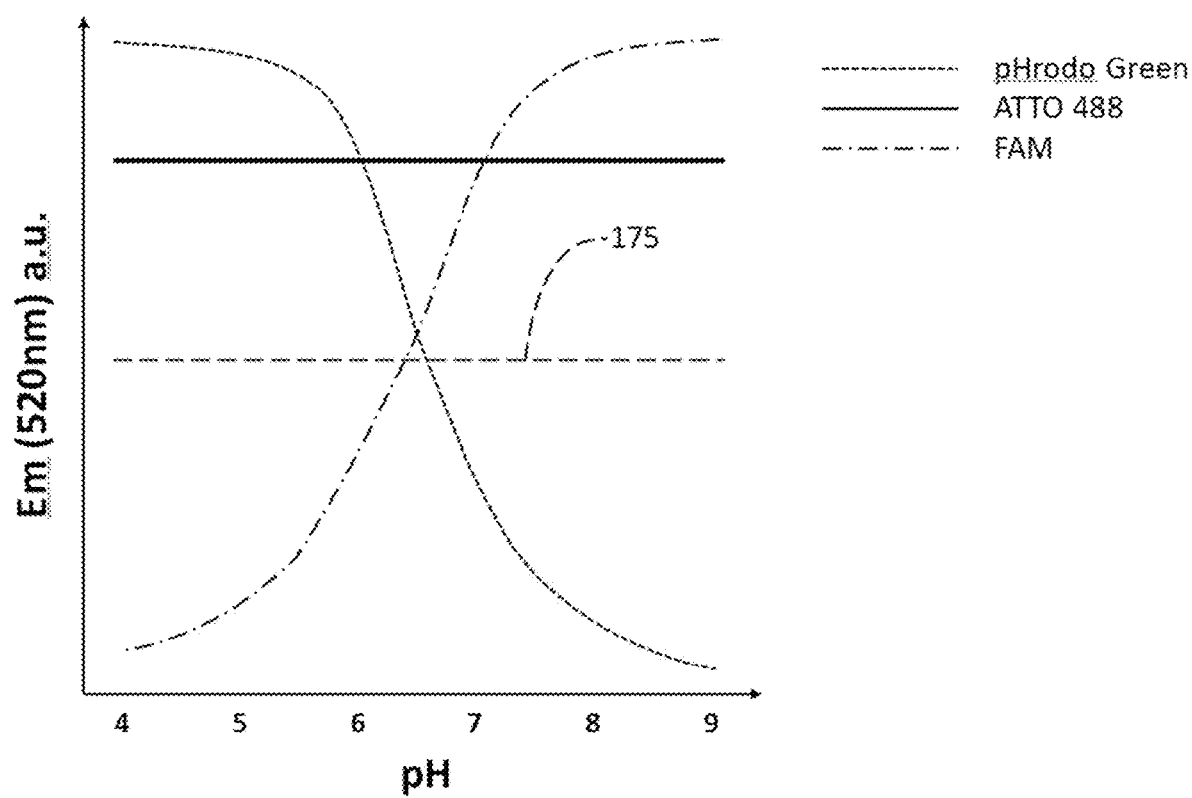
FIG. 2 is a graph of light or emission output versus pH for three dyes, two of which are suitable for use with the ELISA system of FIG. 1, including pHrodo® Green and FAM.

As referred to herein, the tag 174 is "activated" when the tag 174 is located in a reagent solution 150 having a pH that causes the tag 174 (i.e. the pH-sensitive reporter) to emit an intensity of light that is equal to or that exceeds a predetermined light level 175 (FIG. 2). The tag 174 is "deactivated" when the tag 174 is located in a reagent solution 150 having a pH that causes the tag 174 to emit an intensity of light that is less than the predetermined light level 175.

FIG. 2 illustrates the magnitude of fluorescent emissions of exemplary tags 174 including pHrodo Green and FAM versus pH. ATTO 488 dye is also graphed as a control and does not exhibit a change in fluorescent emissions based on pH. As shown in FIG. 2, pHrodo Green has high fluorescent emissions above the predetermined light level 175 when the reagent solution 150 is acidic and low fluorescent emissions below the predetermined light level 175 when the reagent solution 150 is basic. pHrodo Green exhibits a light intensity output that is well above the predetermined light level 175 at a pH in a range of about 4.0 to 5.0. Whereas, FAM has the inverse light intensity output characteristics of pHrodo Green. Specifically, FAM exhibits low fluorescent emissions below the predetermined light level 175 when the reagent solution 150 is acidic and high fluorescent emissions above the predetermined light level 175 when the reagent solution 150 is neutral or basic. FAM exhibits a light intensity output that is well above the predetermined light level 175 at a pH in a range of about 7.5 to 9.0. Based on the above, pHrodo Green appears to glow brightly to an observer when the pH of the reagent solution 150 is about 4.0 to 6.5, and pHrodo Green appears to glow less brightly or not at all when the pH of the reagent solution 150 is greater than about 6.5. FAM appears to glow brightly to an observer when the pH of the reagent solution 150 is about 6.5 to 9.0, and FAM appears to glow less brightly or not at all when the pH of its solution is less than about 6.5.

With reference again to FIG. 1, the power source 116 of the system 100 is an electrical power source that is electrically connected to the electrodes 140, 144 through the controller 132. The power source 116 outputs AC or DC power (as selected by the user) to the electrodes 140, 144 and is provided as any typical power source. In one embodiment, the power source 116 is a switched-mode power supply. The power source 116, in one embodiment, generates and supplies the electrodes 140, 144 with an electrical signal for modulating the pH of only a select portion of the reagent solution 150 (i.e. the portion of the reagent solution 150 located below the modulation line 184, for example).

The memory 124 of the system 100 is a non-transient computer readable medium that is electrically connected to the controller 132. In one embodiment, the memory 124 stores data in program files or programs 180 that correspond to a particular well 108, electrode 140, 144, reagent solution 150, target substance 158, capture agent 166, detection agent 170, and/or tag 174. For example, a first program 180 may include data that causes the power source 116 to supply the electrode 140 with an electrical signal that results in a 2.5 μA current through the sample 134. In one embodiment, the current flows from the electrode 140 through the sample 134 and to the electrode 144, according to conventional current flow. The magnitude of the current is typically selected to correspond to a desired predetermined pH of the reagent solution 150 near the electrodes 140, 144 (i.e. below the modulation line 184 (FIG. 1)). Another program 180 may correspond to a different well 108, electrode 140, 144, reagent solution 150, target substance 158, capture agent 166, detection agent 170, and/or tag 174 and may include data that corresponds to a different desired magnitude of current through the sample 134. Yet another program 180 may operate the system 100 according to a galvanostatic mode or a potentiostatic mode.

The controller 132 is configured to execute the programs/instructions 180 (i.e. software) stored in the memory 124. The controller 132 is operably connected to the power source 116, the memory 124, and the electrodes 140, 144. The controller 132 is provided as at least one microcontroller and/or microprocessor.

Figure 3:
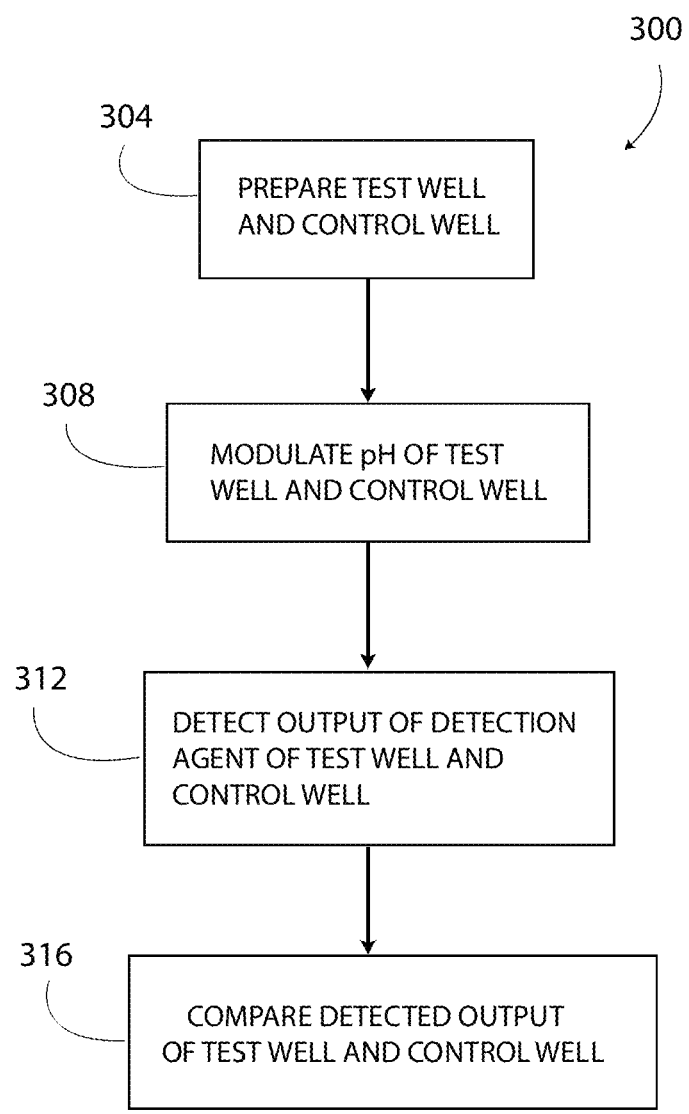
FIG. 3 is a flowchart illustrating an exemplary method for operating the ELISA system of FIG. 1.
Figure 4:
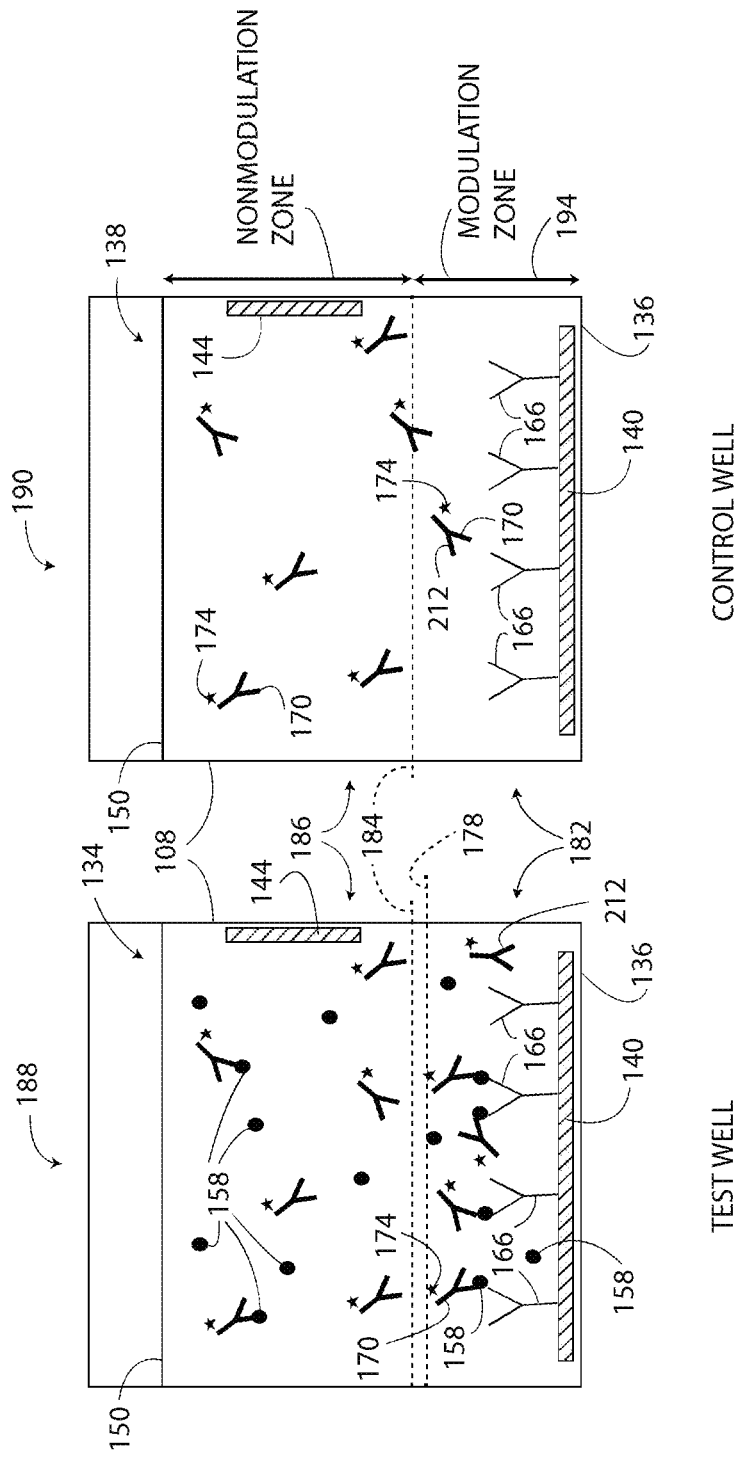
FIG. 4 is a block diagram of a test well and a control well of the ELISA system of FIG. 1, with the ELISA system not exhibiting the localized change in pH.

In operation and with reference to FIG. 3, the controller 132 is configured to execute the method 300 for determining or detecting the presence of the target substance 158 in the sample 134 and/or the concentration of the target substance 158 in the sample 134. As shown in block 304 and with additional reference to FIG. 4, the method 300 includes preparing a test well 188 and a control well 190. The test well 188 and the control 190, in one embodiment, are both one of the wells 108, as described above. To prepare the wells 188, 190, the capture agent 166 is formed on the respective electrodes 140 and is blocked from other areas and surfaces of the wells 188, 190. FIG. 4 illustrates that each well 188, 190 has the capture agent 166 bound or otherwise affixed to the electrode 140.

After the capture agent 166 is bound to the respective electrodes 140, the wells 188, 190 are typically washed to remove any unbound capture agent 166. Washing the wells 188, 190 includes rinsing the wells 188, 190 with reagent solution 150 (or another suitable substance) to remove any unbound molecules of the capture agent 166 from the wells 188, 190. Washing the wells 188, 190 does not disturb or displace the molecules of capture agent 166 bound to the electrode 140. The method 300 has no other washing step.

Next, to prepare further the wells 188, 190, samples are added to each well 188, 190. In particular, the sample 134 is added to the test well 188. The sample 134 includes the reagent solution 150, the target substance 158, and the detection agent 170. A control sample 138 is added to the control well 190. The control sample 138 includes the reagent solution 150 and the detection agent 170, but does not include the target substance 158. In one embodiment, both of the wells 188, 190 include the same reagent solution 150 and the same detection agent 170.

After adding the test sample 134 to the test well 188, as shown in FIG. 4, the molecules of capture agent 166 adsorb, complex, and/or otherwise immobilize at least some molecules of the target substance 158. Moreover, at least some molecules of the detection agent 170 bind to the adsorbed molecules of the target substance 158 and also become immobilized, and other molecules of the detection agent 170 bind to unbound molecules of the target substance 158 and are free-floating in the sample 134. Such process is the "single reaction step" of the method 300. The immobilized molecules of the target substance 158 in the test well 188 are the "detectable molecules" of the target substance 158 using the method 300 and the system 100. The molecules of the target substance 158 that are not immobilized in the test well 188, if any, are typically not detectable by the method 300 and the system 100, even if the detection agent 170 is bound thereto.

After adding the control sample 138 to the control well 190, as shown in FIG. 4, nothing, or nothing of consequence, is immobilized by the capture agent 166 of the control well 190. In the control well 190, there is no target substance 158 to bind to the capture agent 166. Moreover, the detection agent 170 binds directly to the target substance 158 only and cannot bind directly to the capture agent 166. Thus, the control sample 138 includes a substantially homogenous mixture of the detection agent 170, with some molecules of the detection agent 170 located above the modulation line 184 and with other molecules of the detection agent 170 located below the modulation line 184.

Next, as shown in block 308 of FIG. 3, the method 300 includes locally modulating the pH of the samples 134, 138 in both the test well 188 and the control well 190. "Locally" modulating the pH includes changing the pH of only the portion of the reagent solution 150 (i.e. a first portion of the reagent solution 150) located in a respective modulation zone 182 (FIG. 4) of each of the wells 188, 190 from a first pH value (i.e. an unmodulated or an initial pH value, a first value of pH) to a second pH value (i.e. a predetermined pH value, a second value of pH) that is different from the first pH value. In one embodiment, the modulation zone 182 extends from the bottom surface 136 of the well 108 to the modulation line 184 (FIG. 4) located a predetermined distance 194 (FIG. 4) from the bottom surface 136. The modulation line 184 separates the modulation zone 182 from a non-modulation zone 186 (FIG. 4) (i.e. a second portion of the reagent solution 150). The pH of the reagent solution 150 in the non-modulation zone 186 is not changed when the pH of the reagent solution 150 in the modulation zone 182 is locally modulated (i.e. changed). That is, during local modulation of the pH, the portion of the samples 134, 138 located below the modulation line 184 in the modulation zone 182 is modulated, and the pH of the portion of the samples 134, 138 located above the modulation line 184 in the non-modulation zone 186 is not modulated (or is prevented from being modulated). Locally modulating the pH is also referred to herein as (i) changing the ionic concentration of the reagent solution 150 in the modulation zone 182 by electrochemical reaction, and (ii) introducing an ionic gradient in at least the sample 134 at and below the modulation line 184.

The pH of the reagent solution 150 is locally modulated by exciting the electrodes 140, 144 according to at least one of the programs 180 (FIG. 1) stored in the memory 124 (FIG. 1). In one embodiment, the excited electrode 140 causes an in situ oxidation and/or reduction of the portion of the reagent solution 150 located near the electrode 140 in the modulation zone 182. The oxidation and/or reduction either (i) liberates hydrogen ions (H+) which bond to water molecules of the aqueous reagent solution 150 to form hydronium cations ($H_3O^+$) that acidify the reagent solution 150 (i.e. locally decreasing the pH), or (ii) increases the concentration of hydroxide anions ($OH^-$) that alkalize the reagent solution 150 (i.e. locally increasing the pH). The system 100 is configurable to increase locally or to decrease locally the pH of the reagent solution 150 in the modulation zone 182 based on at least the composition of the reagent solution 150, the composition of the electrodes 140, 144, the surface structure of the electrodes 140, 144 (i.e. are the electrodes 140, 144 patterned), and characteristics of the electrical signal applied to the electrodes 140, 144 from the controller 132.

Figure 5:
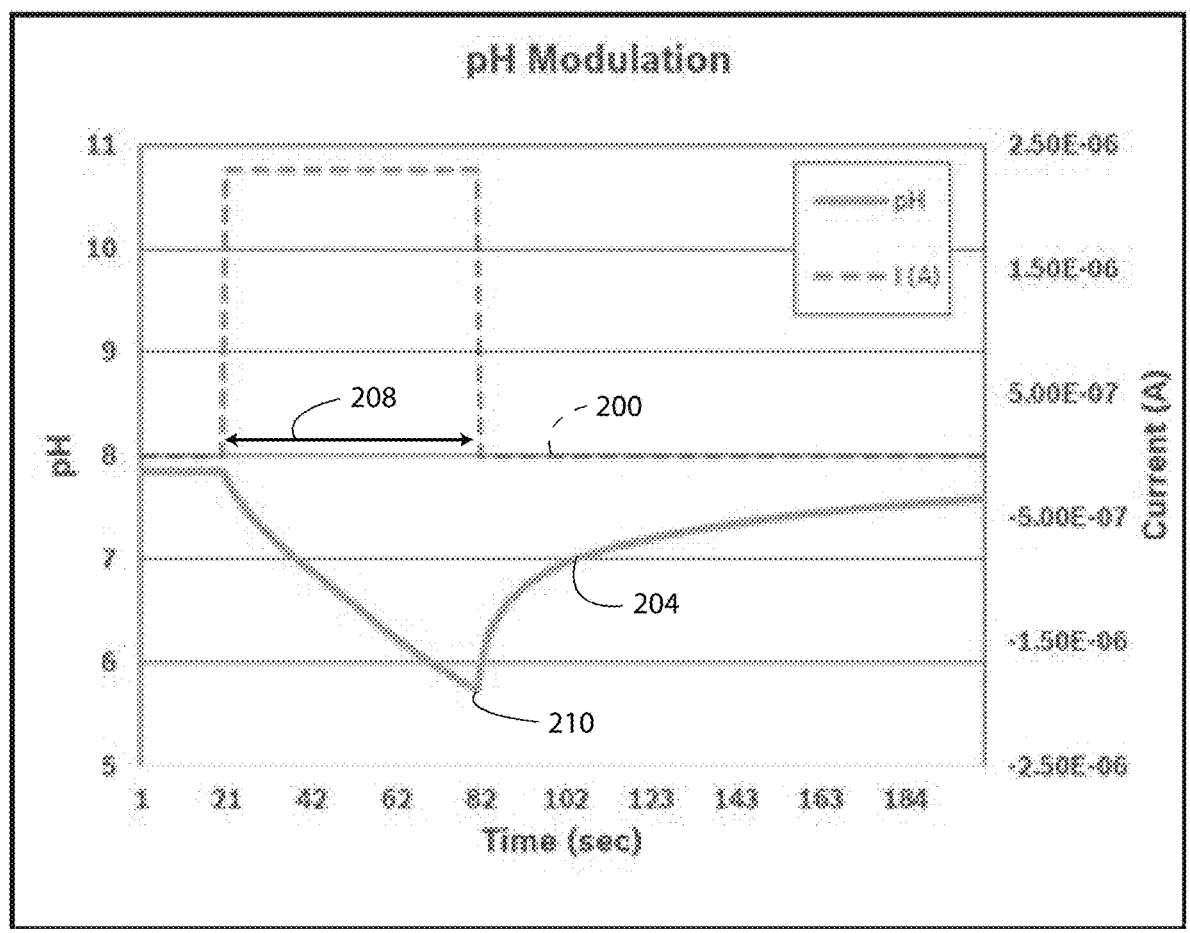
FIG. 5 is a graph of electrical current and pH versus time associated with the ELISA system of FIG. 1.

The graph of FIG. 5 illustrates an electrical signal 200 suitable for application to the respective electrodes 140, 144 and a pH curve 204 representing the locally modulated pH of the reagent solution 150 in the modulation zone 182 in response to the electrical signal 200. More specifically, FIG. 5 demonstrates the on-demand pH modulation by the oxidation of 2,5-dimethyl hydroquinone on an indium-tin oxide electrode 140 in a reagent solution 150 having a 1 mM phosphate buffer. When anodic current (i.e. the electrical signal 200) is applied to the electrode 140, proton production overcomes the buffer capacity of the reagent solution 150 and the pH of the reagent solution 150 becomes more acidic. The electrical signal 200 is measured as an electrical current that is 0 microamps (0 µA) from time 0 to 21 seconds and then is increased as a step function to approximately 2.4 microamps (2.4 µA). The electrical signal 200 energizes the electrode 140 with a direct current electrical signal of 2.4 microamps for a predetermined time period 208 of about 60 seconds. After the predetermined time period 208, the electrical signal 200 steps down to 0 microamps. In other embodiments, the predetermined time period 208 is from 1.0 nanosecond to 60 minutes. The pH values of the pH curve 204 in FIG. 5 were determined by a pre-calibrated iridium oxide sensing electrode (not illustrated) patterned on the surface.

In response to the electrical signal 200 applied to the electrode 140, the portion of the reagent solution 150 located in the modulation zone 182 exhibits a temporary change in pH. As shown in the pH curve 204 of FIG. 5, the pH changes from an initial value of about 8.0 to a predetermined pH value 210 (FIG. 5) of about 5.7. The pH of the portion of the reagent solution 150 in the modulation zone 182 is gradually reduced to the predetermined pH 210 over the course of the predetermined time period 208. In one embodiment, the reagent solution 150 exhibits a substantially linear reduction in pH in response to the electrical signal 200, as shown in FIG. 5. The reduction in pH of the reagent solution 150 depends on at least the characteristics of the electrical signal 200, the composition of the reagent solution 150, and the buffer strength. The reduction in pH of the reagent solution 150 is non-linear in other embodiments. At the end of the predetermined time period 208 when the electrical signal 200 is no longer applied to the electrode 140, the pH of the reagent solution 150 in the modulation zone 182 reverts back to the initial value. FIG. 5 shows that the reversion to the initial value is substantially exponential, much like the charging of a capacitor. The pH of the reagent solution 150 in the modulation zone 182, in one embodiment, reverts back to the initial value of pH in about five minutes. The time required for the pH of the reagent solution 150 to revert back to the initial value of pH is dependent on at least the characteristics of the electrical signal 200, the composition of the reagent solution 150, and the buffer strength. Accordingly, the pH of the reagent solution may revert back to the initial value of pH in anywhere from one second to ten minutes.

The local modulation of the pH of the reagent solution 150 can be carried out in a galvanostatic mode (current controlled) or a potentiostatic mode (voltage controlled). Moreover, any type of electrical signal can be applied to the electrodes 140, 144 during the method 300. For example, the electrical signal applied to the electrodes 140, 144, in one embodiment, is an annealing pulse having a predetermined pulse frequency, a predetermined pulse width, and a predetermined pulse shape. The voltage of the annealing pulse is sufficient to change the pH in the modulation zone 182, and to remove non-covalently bound molecules from the sample 134. The removal of the non-covalently bound molecules eliminates or reduces a washing of the substrate (i.e. the electrode 140) following the initial contact between the target substance 158 and the capture agent 166. Another advantage is that the annealing pulse is more efficient at removing non-covalently bound material from the sample 134 than a simple washing.

The local modulation of the pH of the reagent solution 150 can also be carried out with closed-loop control. Closed-loop control provides precise pH control of the reagent solution 150 utilizing a closed-loop control function that is based on an input from a pH sensor (not shown) located in the well 108. The magnitude of the electrical signal 200 applied to electrodes 140, 144 may be dynamically adjusted using the closed-loop control so that a desired pH level of the reagent solution 150 in the modulation zone 182 is maintained for the predetermined time period 208.

The method 300 enables the system 100 to control the quantity of the reagent solution 150 that undergoes the local change in pH. Such control is visualized and understood by considering that the controller 132 controls the location of the modulation line 184 within the wells 188, 190. The location of the modulation line 184 is typically measured as the distance between the modulation line 184 and the electrode 140, 144 on which the capture agent 166 is located. The location of the modulation line 184 is selected based at least in part on the immobilized height line 178 (FIG. 4). In one embodiment, the location of the modulation line 184 is determined to be at the same location as the immobilized height line 178 or just slightly further from the electrode 140 than the immobilized height line 178 (i.e. higher than the immobilized height line 178). The location of the modulation line 184 is the same for both the test well 188 and the control well 190 even though the control well 190 does not include immobilized molecules of the target substance 158.

The electrical signal applied to the electrode 140 causes the oxidation/reduction reaction of the reagent solution 150 to occur at the electrode 140. During the predetermined time period 208, the pH changing ions and/or anions formed at the surface of the electrode 140 diffuse away (upward in FIG. 4) from the electrode 140. The result is that the modulation line 184 can be thought of as starting at the level of the electrode 140 and moving upward away from the electrode 140 during the predetermined time period 208. As the duration of the predetermined time period 208 increases, the height of the modulation line 184 increases and the amount of the reagent solution 150 that undergoes the local change in pH increases. In another embodiment, the location of the modulation line 184 is determined, at least in part, by the configuration of the electrodes 140, 144, specifically by the magnitude of the electrical signal applied to the electrodes 140, 144.

The duration of the predetermined time period 208 is selected, in one embodiment, so that only the portion of the reagent solution 150 located from the immobilized height line 178 to the bottom surface 136 of the well undergoes the change in pH. That is, the duration of the predetermined time period 208 is at least long enough for the pH changing ions and/or anions to diffuse from the surface of the electrode 140 upward to the immobilized height line 178 so that the molecules of the detection agent 170 that are bound to the capture agent 166 through the target substance 158 are located in the region of modulated pH. To this end, the modulation line 184 is configured to be very close (i.e. from 1-100000 nanometers) to a surface formed by an average height of the immobilized target substance 158 and detection agent 170 on the capture agent 166 (i.e. very close to the immobilized height line 178).

As described above, the tags 174 of the detection agent 170 are pH-sensitive. The method 300 results in the tags 174 located in the modulation zone 182 undergoing a change, and prevents the tags 174 located in the non-modulation zone 186 from undergoing the change. Specifically, the controller 132 causes only the tags 174 located in the modulation zone 182 to emit light above the predetermined light level 175, and prevents the tags 174 located in the non-modulation zone 186 from emitting light above the predetermined light level 175 or to emit light below the predetermined light level 175. The controller 132 causes only the tags 174 located at or below the immobilized height line 178 to emit light, because only these tags 174 potentially indicate the presence of the target substance 158. The method 300 includes operating the controller 132 to supply at least the electrode 140 with the electrical signal 200 for the predetermined time period 208, which is of sufficient duration to cause the pH of the reagent solution 150 located at or below the immobilized height line 178 to change to the predetermined pH 210 and to cause the tags 174 located in the modulation zone 182 to undergo the detectable change. Thus, the method 300 includes using dynamic and on-demand control over the pH of the reagent solution 150 in the modulation zone 182.

Block 312 in FIG. 3 shows that the method 300 includes detecting an output signal of the detection agent 170 in the test well 188. The detection agent 170 may have any suitable output type or output signal including luminescence, fluorescence, colorimetric methods, electrochemical methods, impedance measurements, magnetic induction measurements, and/or chemiluminescent. In one embodiment, the method 300 includes detecting the brightness and/or the intensity of the light emitted from the test well 188 as a first detected value (i.e. a first change of the tags 174 and a first output signal) and detecting the brightness and/or the intensity of the light emitted from the control well 190 as a second detected value (i.e. a second change of the tags 174 and a second output signal). The detected values are detected when the portion of the reagent solution 150 in the modulation zone 182 is exhibiting the predetermined pH 210.

Figure 6:
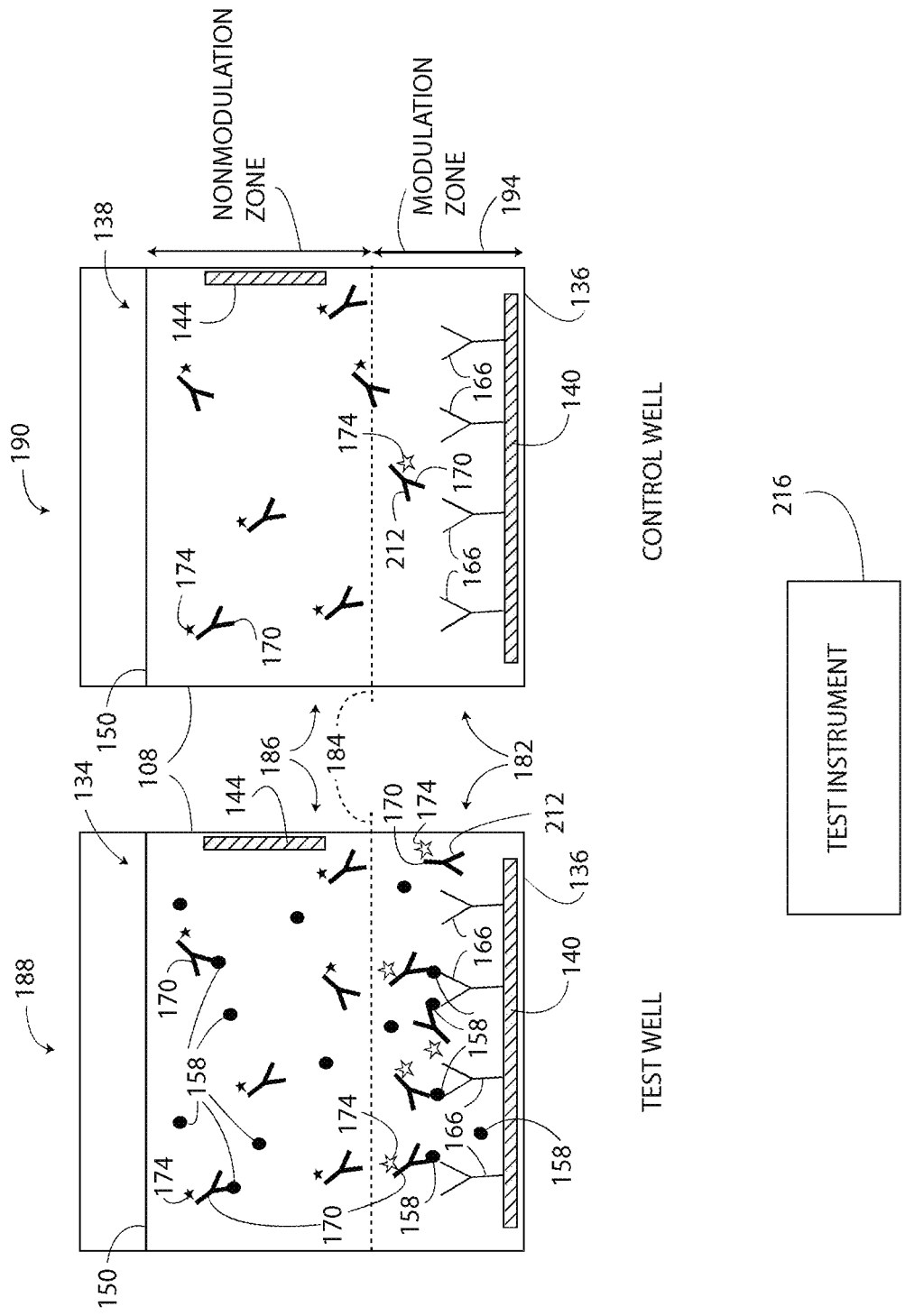
FIG. 6 is a block diagram of the test well and the control well of the ELISA system of FIG. 1, with the system exhibiting the localized change in pH in both the test well and the control well.

As shown in FIG. 6, when the reagent solution 150 changes to the predetermined pH, the tags 174 of the detection agents 170 located at or below the modulation line 184 exhibit a detectable change that is detectable with a test instrument, such as a charge-coupled device, a camera, an infrared camera, a thermal camera, a spectrophotometer, a fluorometer, a luminometer, a microscope, and/or the human eye. The tags 174 having undergone the detectable change are illustrated as white stars with a black outline in FIG. 6, and the tags 174 not having undergone the detectable change are illustrated as solid black stars in FIG. 6. In FIG. 6, only the tags 174 located in the modulation zone 182 exhibit the detectable change, and the tags 174 that are not in the modulation zone 182 (i.e. that are in the non-modulation zone 186) do not exhibit the detectable change. The detectable change occurs in the tags 174 of the test well 188 and the tags 174 of the control well 190 that are located in the modulation zone 182.

FIG. 6 further illustrates that some molecules of the detection agent 170 that are located below the modulation line 184 are not bound (directly or indirectly) to the capture agent 166. These unbound molecules (i.e. free floating molecules) of detection agent 170 located below the modulation line 184 contribute to the detectable change in brightness, but do not indicate the presence of the target substance 158 and are referred to hereinafter as false detection molecules 212. Both the test well 188 and the control well 190 typically include at least some false detection molecules 212 because the molecules of the detection agent 170 are dispersed throughout the reagent solution 150. Moreover, due to the similar structure, shape, and size, the wells 188, 190 typically include the same number of the false detection molecules 212. Thus, the first detected value is a sum of the bound portion of the detection agent 170 and the unbound portion of the detection agent 170 located in the modulation zone 182 of the test well 188. The second detected value is the unbound portion of the detection agent 170 located in the modulation zone 182 of the control well 190. The controller 132 accounts for the false detection molecules 212, as described below. Moreover, above the modulation line 184, all or substantially all of the molecules of the detection agent 170 are unbound to the capture agent 166 and do not undergo a change because they are not exposed to the modulated pH of the modulation zone 182.

Next, as shown in block 316, the method 300 includes using the controller 132 to compare the detected value of the test well 188 to the detected value of the control well 190 to generate another output signal. In one embodiment, an electronic test instrument 216 (FIG. 6) is used to detect the detected values of the test well 188 and the control well 190 and to subtract the second detected value of the control well 190 from the first detected value of the test well 188 to arrive at a test value of the system 100. The subtraction isolates the light output of the bound detection agent 170 located in the modulation zone 182 of the test well 188 from the light output of the unbound detection agent 170 located in the modulation zone 182 of the test well 188. The output of the test instrument 216, in one embodiment, is calibrated to represent the concentration or quantity of the target substance in the sample 134. Additionally or alternatively, the output of the test instrument 216 is an indication of only the presence or the absence of the target substance 158 in the sample 134.

In an example, as shown in FIG. 6, the test well 188 includes the target substance 158 and the control well 190 does not include the target substance 158. The detected value of the test well 188 includes the light output of the detection agent 170 bound to the target substance 158 plus the light output of the false detection molecules 212. The detected value of the control well 190 includes only the light output of the false detection molecules 212. Since the sample 134 and the sample 138 are substantially the same except for the addition of the target substance 158 to the sample 134, both samples 134, 138 should have the same number of the false detection molecules 212. Thus, subtracting the light output of the control well 190 from the light output of the test well 188 removes the effects of the false detection molecules 212 from the light output of the test well 188, and the difference represents only the light output of the detection agent 170 that is bound to the target substance 158 in the test well 188.

In another example, not shown in the figures, the test well 188 does not include the target substance 158 (a fact that might be initially unknown to the technician) and the control well 190 does not include the target substance 158. In this example, the detected value of the test well 188 is based on only the light output of the false detection molecules 212 and the detected value of the control well 190 is based on only the light output of the false detection molecules 212. Thus, when the detected value of the control well 190 is subtracted from the detected value of the test well 188 the difference is approximately zero, thereby indicating that the target substance 158 is not present in the test well 188.

In another embodiment, blocks 312 and 316 of the method 300 are performed by a technician in a point-of-care solution. In this embodiment, the tags 174 of the detection agent 170 are configured to emit light in the visible (to the human eye) spectrum. During block 312, the technician observes the respective brightness levels or the particular colors of the test well 188 and the control well 190. Then, the technician compares the brightness levels and/or the colors to a printed or an electronic reference chart (for example) to determine results of the test (i.e. to determine the presence and/or concentration of the target substance 158 in the sample 134). No electronic test instrument 216 is used in this embodiment to determine the test results.

In yet another embodiment of the single-step ELISA system 100, a detection window small enough to cover only a set of complete binding complex of a capture agent 166, a target substance 158, and a detection agent 170 labeled with pH-sensitive signal reporting system (fluorescent dye-based or enzyme-based) is utilized so that a noise signal from unbound detection antibodies (i.e. the false detection molecules 212) is effectively excluded. For this purpose, the pH modulation step is typically quick and the physical space that the active pH modulation occurs is typically well controlled.

Figure 7:
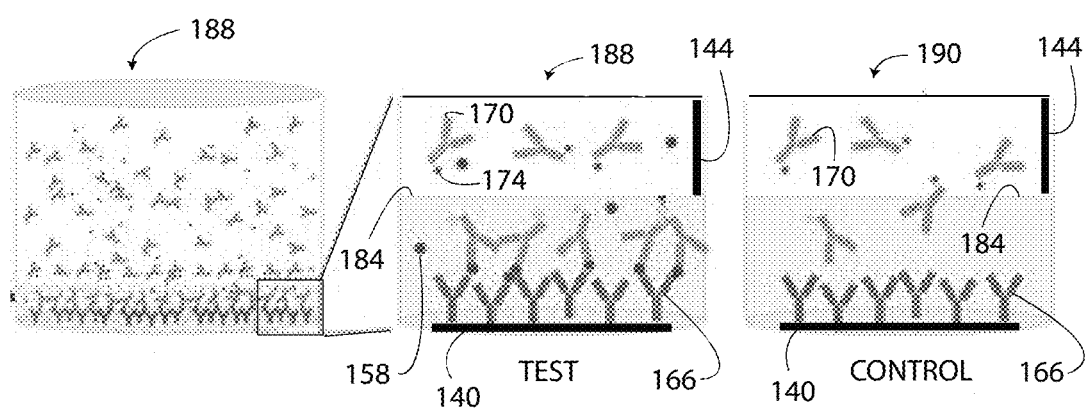
FIG. 7 is a block diagram illustrating an exemplary signal readout of the ELISA system of FIG. 1.

FIG. 7 includes another illustration of the test well 188 and the control well 190 with a different arrangement of the capture agent 166, the target substance 158, and the detection agent 170.

Figure 8:
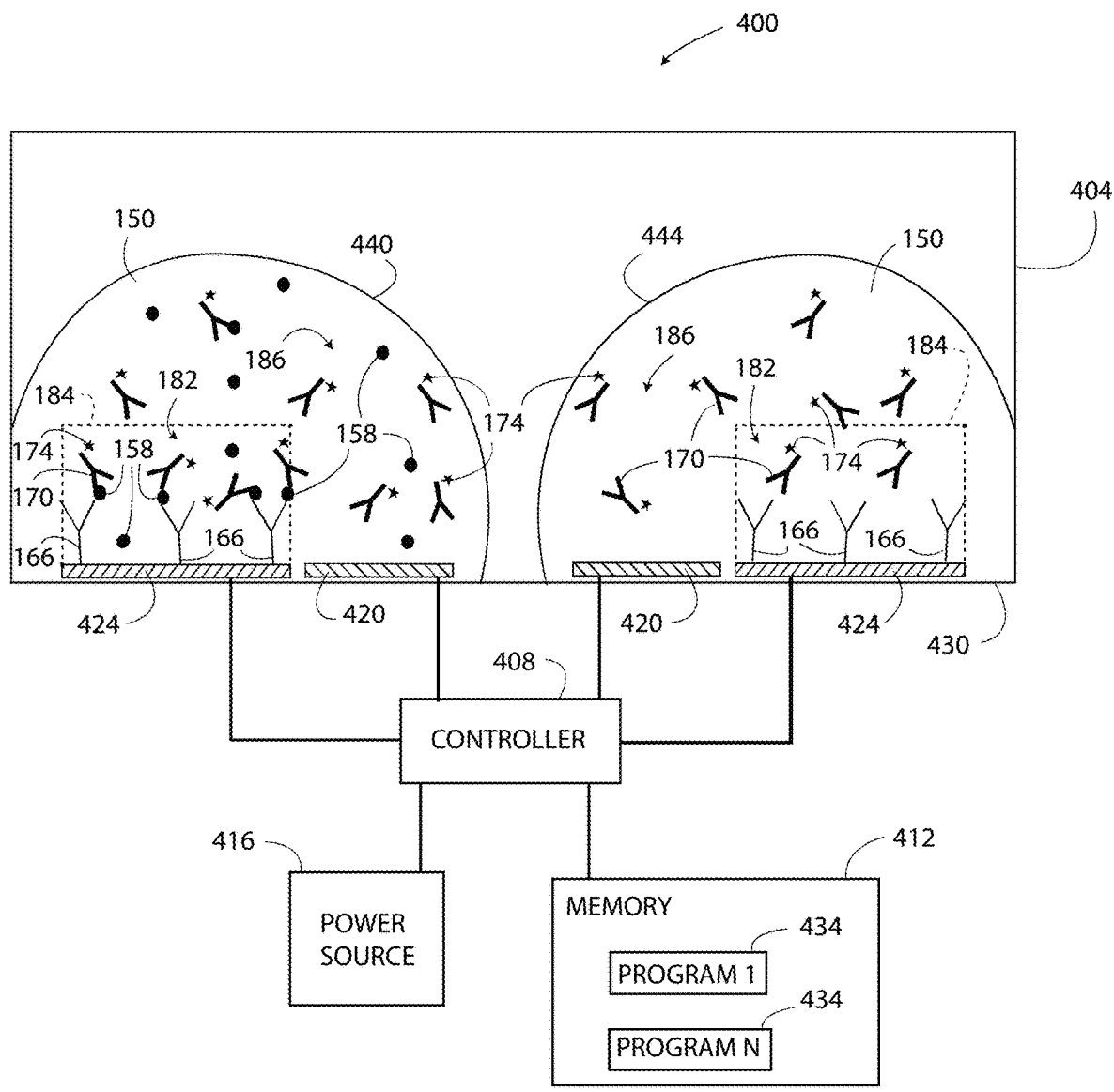
FIG. 8 is a block diagram illustrating an exemplary multiplexed embodiment of a single-step ELISA system.

As shown in FIG. 8, a multiplexed embodiment of a single-step ELISA system 400 includes a well 404, a controller 408, a memory 412, and a power source 416. The well 404 has electrodes 420 and electrodes 424 located therein. Each of the electrodes 420, 424 is located on a bottom surface 430 of the well 404. The electrodes 420, 424, the power source 416, and the memory 412 are each electrically connected to the controller 408. The memory 412 includes programs 434 configured to cause the controller 408 to implement a method similar to the method 300 of FIG. 3. The controller 408 is substantially the same as the controller 132, the power source 416 is substantially the same as the power source 116, and the memory 412 is substantially the same as the memory 124. FIG. 8 illustrates that a test sample 440 is located on the left set of the electrodes 420, 424 and a control sample 444 is located on the right set of the electrodes 420, 424. A physical space (i.e. a gap) is located between the samples 440, 444, such that the samples 440, 444 are isolated from each other by an air space.

The system 400 differs from the system 100 in that the test sample 440 and the control sample 444 are located in the same well 404 (i.e. in the same space) in a multiplexed arrangement. As shown in FIG. 8, the volume of the test sample 440 is selected to form a small "bubble" on the left set of the electrodes 420, 444 that does not extend to the right set of the electrodes 420, 444. The surface tension of the test sample 440 maintains the shape of the test sample 440 and prevents the test sample 440 from contacting and mixing with the control sample 444. Similarly, the volume of the control sample 444 applied to the right set of the electrodes 420, 424 is selected to form another small "bubble" that does not extend to the left set of the electrodes 420, 424. The surface tension of the control sample 444 maintains the shape of the control sample 444 and prevents the control sample 444 from contacting and mixing with the test sample 440. As a result, the system 400 uses half the number of wells 404 as compared to the system 100.

In operation, the system 400 includes locally modulating the pH of the test sample 440 and the control sample 444 in the well 404. In the illustrated embodiment, the modulation zone 182 is defined by the modulation lines 184 and is a substantially rectangular area of the reagent solution 150 located above the electrode 424. The capture agent 166 is located in the modulation zone 182. The modulation lines 184 separate the modulation zone 182 from a non-modulation zone 186. The pH of the reagent solution 150 in the non-modulation zone 186 is not changed when the pH of the reagent solution 150 in the modulation zone 182 is locally modulated. The pH of the reagent solution 150 is locally modulated by the controller 408 by exciting the electrodes 420, 424 according to the process set forth above.

In FIG. 8, the tags 174 of the detection agent 170 are pH-sensitive, and the tags 174 located in the modulation zone 182 undergo a change in response to the locally modulated pH. The tags 174 located in the non-modulation zone 186 do not undergo the change. The change undergone by the tags 174 located in the modulation zones 182 of FIG. 8 forms two output signals. Only the tags 174 located in the modulation zone 182 contribute to the output signal of the test sample 440, and the tags 174 located outside of the modulation zone 182 do not contribute to the output signal. Specifically, only the tags 174 located in the modulation zones 182 emit light above the predetermined light level 175, and the tags 174 located in the non-modulation zones 186 are prevented from emitting light above the predetermined light level 175 or emit light below the predetermined light level 175. The tags 174 located outside of the zone 182 defined by the modulation line 184 of the test sample 440 cannot indicate the presence of the target substance 158 because these tags 174 do not generate any type of output signal in response to the locally modulated pH. The light output of the tags 174 located in the modulation zone 182 of the test sample 440 is detected as a first detected value, and the light output of the tags 174 located in the modulation zone 182 of the control sample 444 is detected as a second detected value. The controller 408 compares the detected value of the test sample 440 to the detected value of the control sample 444, according to the process set forth above to determine the presence and/or concentration of the target substance 158 in the test sample 440.

Figure 9:
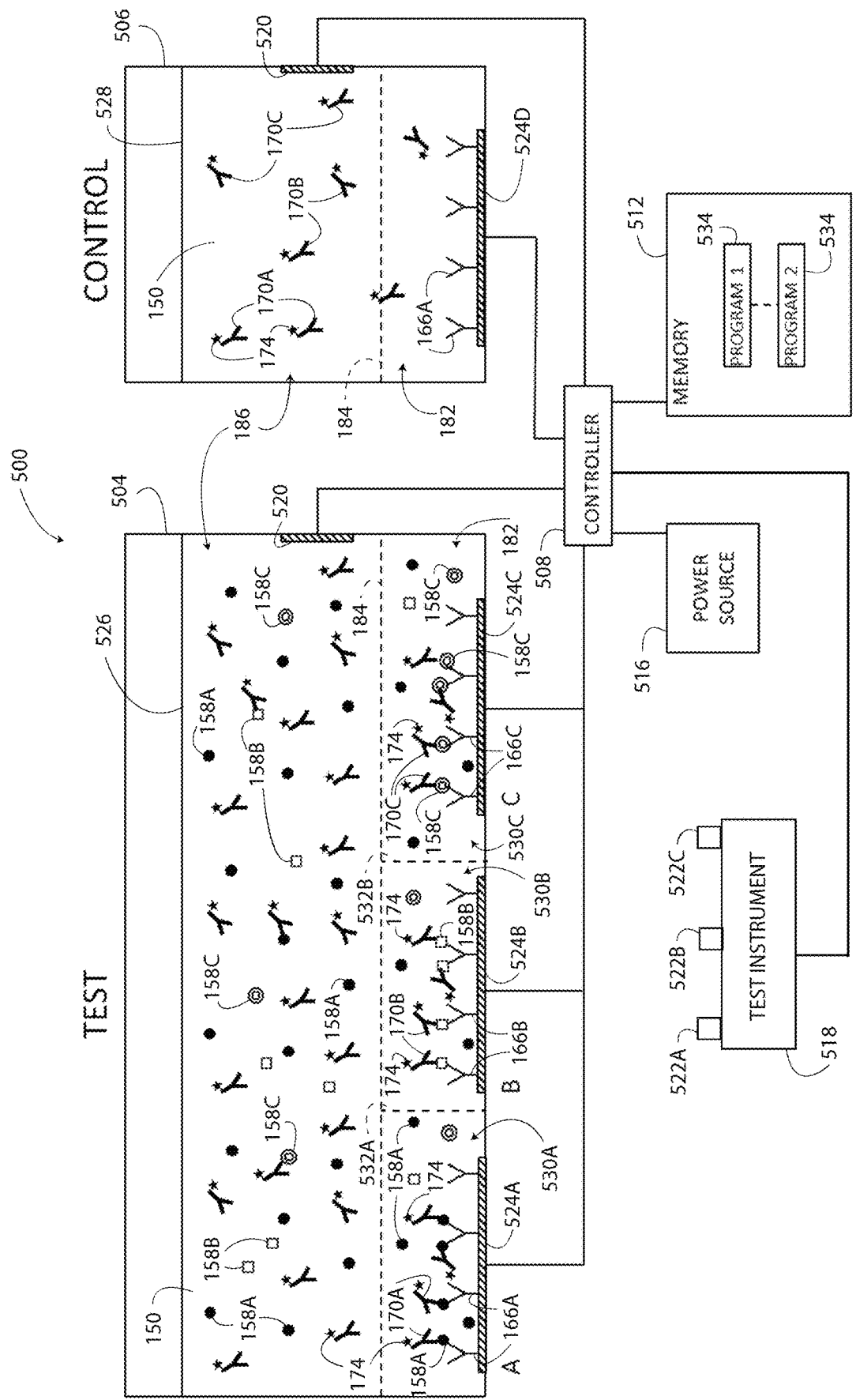
FIG. 9 is a block diagram illustrating another exemplary multiplexed embodiment of a single-step ELISA system.

Another multiplexed single-step ELISA system 500 is shown in FIG. 9. The system 500 is configured to detect the presence and/or concentration of multiple/different types of target substances 158A, 158B, 158C within a single a test sample 526. The system 500 includes a test well 504, a control well 506, a controller 508, a memory 512, a power source 516, and a test instrument 518 having three sensors 522A, 522B, 522C. The test well 504 includes a common electrode 520 shared by electrodes 524A, 524B, 524C, and the test sample 526 located therein. The control well 506 includes electrodes 520, 524D and a control sample 528 is located therein. The electrodes 524A, 524B, 524C, 524D, 520, the memory 512, the power source 516, and the test instrument 518 are each electrically connected to the controller 508. The memory 512 includes programs 534 configured to cause the controller 508 to implement a method similar/the same as the method 300 of FIG. 3. The controller 508 is substantially the same as the controller 132, the power source 516 is substantially the same as the power source 116, and the memory 512 is substantially the same as the memory 124.

The system 500 of FIG. 9 differs from the system 100 in that the test sample 526 includes three different capture agents 166A, 166B, 166C, three different target substances 158A, 158B, 158C, and three different detection agents 170A, 170B, 170C within the reagent solution 150. The target substances 158A, 158B, 158C are each illustrated differently in FIG. 9. The capture agents 166A, 166B, 166C and the detection agents 170A, 170B, 170C are distinguishable by reference numeral and letter in FIG. 9, but have the same graphical depiction. The capture agent 166A is bound to only the electrodes 524A and 524D, the capture agent 166B is bound to only the electrode 524B, and the capture agent 166C is bound to only the electrode 524C. The system 500 also differs in that the modulation zone 182 includes substantially rectangular sub-modulation zones 530A, 530B, 530C, as described below.

The exemplary configuration of the test well 504 forms an "A" detection zone on the left side of the test well 504 including the sub-modulation zone 530A, a "B" detection zone in the middle of the test well 504 including the sub-modulation zone 530B, and "C" detection zone on the right side of the test well 504 including the sub-modulation zone 530C. Line 532A identifies a boundary between sub-modulation zone 530A and sub-modulation zone 530B, and line 532B identifies a boundary between sub-modulation zone 530B and sub-modulation zone 520C. In one embodiment, the sensor 522A of the test instrument 518 is positioned to detect light output from the "A" detection zone (i.e. the sub-modulation zone 530A), the sensor 522B is positioned to detect light output from the "B" detection zone (i.e. the sub-modulation zone 530B), and the sensor 522C is positioned to detect light output from the "C" detection zone (i.e. the sub-modulation zone 530C). In other embodiments, the test instrument 518 includes less than three of the sensors 522A, 522B, 522C. For example, in one embodiment, the test instrument 518 includes a "wide angle" sensor (not shown) that is configured detect and to differentiate the light output from each of the detection zones A, B, C. Each embodiment of the test instrument 518 is also configured to detect the light output from the modulation zone 182 of the control well 506.

The control well 506 includes an exemplary control sample 528 including the reagent solution 150 and at least one type of the detection agents 170A, 170B, 170C. In the exemplary embodiment of FIG. 9, the control sample 528 includes all three of the detection agents 170A, 170B, 170C. At least one of the capture agents 166A, 166B, 166C is bound to the electrode 524D. In the illustrated example, the capture agent 166A is bound to the electrode 524D.

In operation, the system 500 includes locally modulating the pH of the test sample 526 in the well 504 and the control sample 528 in the well 506. In the illustrated embodiment, the modulation zone 182 extends from modulation line 184 downward toward the electrodes 524A, 524B, 524C, 524D. The capture agent 166A is located in the sub-modulation zone 530A, the capture agent 166B is located in the sub-modulation zone 530B, and the capture agent 166C is located in the sub-modulation zone 530C. The modulation line 184 separates the modulation zone 182 from a non-modulation zone 186. The pH of the reagent solution 150 in the non-modulation zone 186 is not changed when the pH of the reagent solution 150 in the modulation zone 182 is locally modulated. The pH of the reagent solution 150 is locally modulated by the controller 508 by exciting at least one of the electrodes 524A, 524B, 524C and the electrode 520 according to the process set forth above.

The tags 174 of the detection agent 170A, 170B, 170C are pH-sensitive, and the tags 174 located in the modulation zone 182 undergo a change in response to the locally modulated pH. The tags 174 located in the non-modulation zone 186 do not undergo the change. The change undergone by the tags 174 located in the modulation zones 182 of FIG. 9 form at least four output signals. The first three output signals are generated at detections zones A, B, and C respectively. The fourth output signal is generated at the modulation zone 182 of the control well 506. Only the tags 174 located in the modulation zone 182 contribute to the output signal of the test sample 526, and the tags 174 located outside of the modulation zone 182 do not contribute to the output signal. In one embodiment, the light output of the tags 174 located in the detection zone A of the test sample 526 is detected as a first detected value, the light output of the tags 174 located in the detection zone B of the test sample 526 is detected as a second detected value, the light output of the tags 174 located in the detection zone C of the test sample 526 is detected as a third detected value, and the light output of the tags 174 located in the modulation zone 182 of the control sample 528 is detected as a fourth detected value. Specifically, the light output (the output signals) of each detection zone A, B, C may be generated simultaneously by energizing each of the electrodes 524A, 524B, 524C simultaneously to modulate the pH in the entire modulation zone 182 including all of the sub-modulation zones 530A, 530B, 530C. In another embodiment, a selected one of the three electrodes 524A, 524B, 524C and/or the electrode 520 are modulated to modulate the pH in only a selected one of the sub-modulation zones 530A, 530B, 530C in which case only the tags 174 located in the selected sub-modulation zone 530A, 530B, 530C undergo the change and generate a light output detectable by the test instrument 518 as a detected value. The controller 508 compares the detected value(s) of the test sample 526 to the detected value of the control sample 528, according to the process set forth above to determine the presence and/or concentration of the target substance 158A, 158B, 158C in the test sample 526.

In another embodiment, the system 500 includes three different types of tags 174 (not shown), such as an A, B, and C type of tag 174. In such an embodiment, each type of tag 174 is configured to generate a unique or individually identifiable (by the test instrument 518) output. For example, when exposed to the predetermined pH value 210 each different type of tag 174 may output light of a different wavelength.

Figure 10:
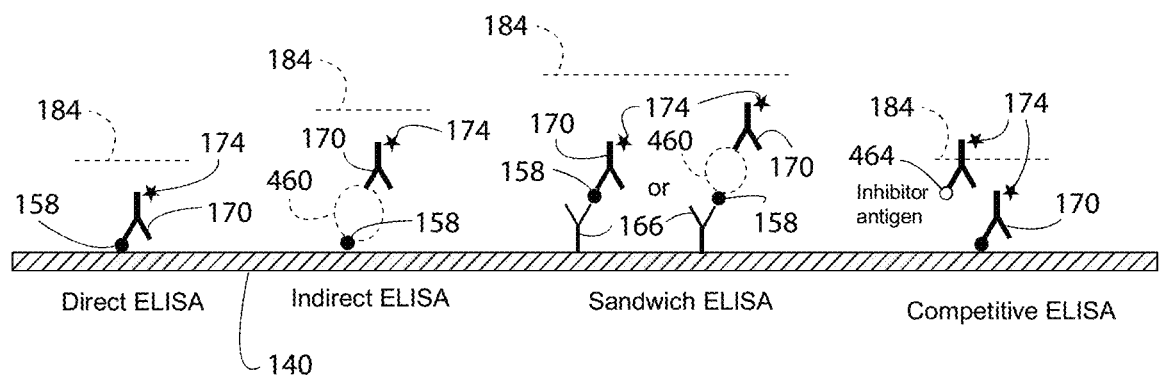
FIG. 10 is a block diagram illustrating four types of ELISA suitable for use with the single-step ELISA systems disclosed herein.
Figure 11:
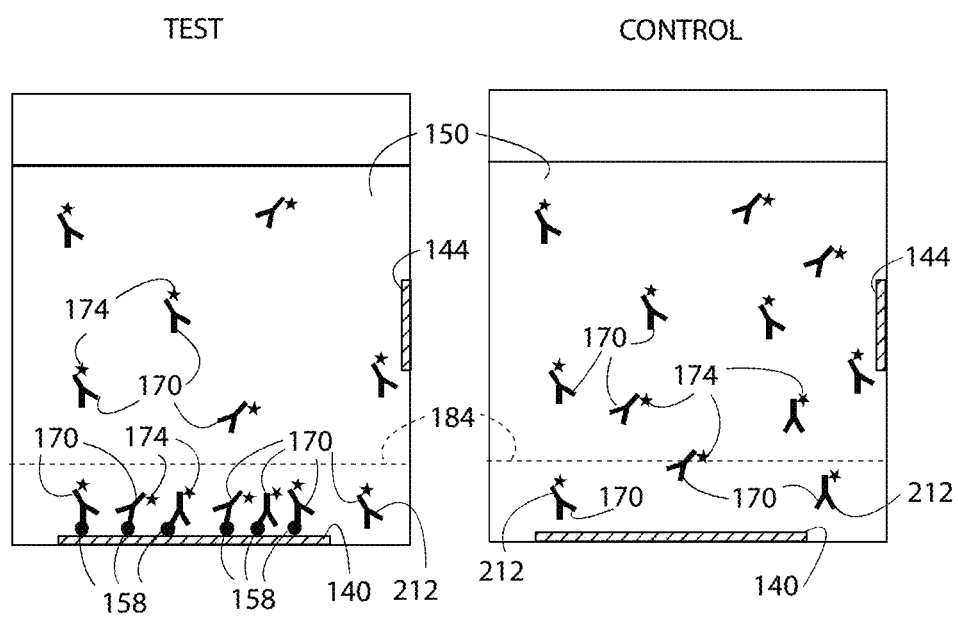
FIG. 11 is a block diagram illustrating another test well and another control well of the ELISA systems disclosed herein.

As shown in FIG. 10, the single-step ELISA systems 100, 400, 500 are compatible with various types of ELISA including "sandwich" ELISA techniques in which the target substance 158 is "sandwiched" between the capture agent 166 and the detection agent 170. In the sandwich technique, an intermediary molecule 460 (shown by a dotted oval) may or may not be bound between the target substance 158 and the detection agent 170. The systems 100, 400, 500 are also compatible with direct ELISA in which a capture agent 166 is not included, and the target substance 158 is bound directly to the electrode 140, 424. Direct ELISA, which is also illustrated in FIG. 11, includes the detection agent 170 bound to the target substance 158, so that the target substance 158 is detected directly. Whereas, in indirect ELISA (shown in FIG. 10) the intermediary molecule 460 is bound between the target substance 158 and the detection agent 170, and the target substance 158 is detected indirectly by measuring the output of the detection agent 170 molecules that have bound to the intermediary molecule 460. Moreover, the systems 100, 400, 500 are compatible with competitive ELISA which does not include the capture agent 166, but does include an inhibitor substance 464, such as an inhibitor antigen. In each type of ELISA, the systems 100, 400, 500 modulate the pH of the reagent solution 150 according to the method 300 described above. The systems 100, 400, 500 are compatible with all types of ELISA.

Figure 12:
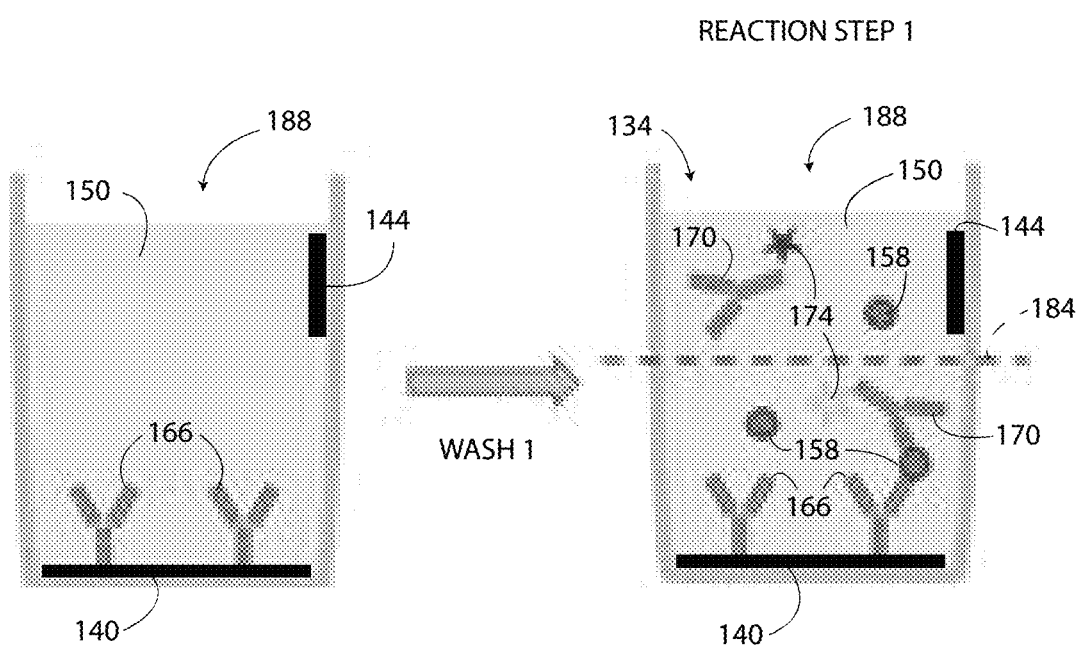
FIG. 12 is a block diagram illustrating the washing step and the single reaction step of the ELISA systems disclosed herein.
Figure 13:
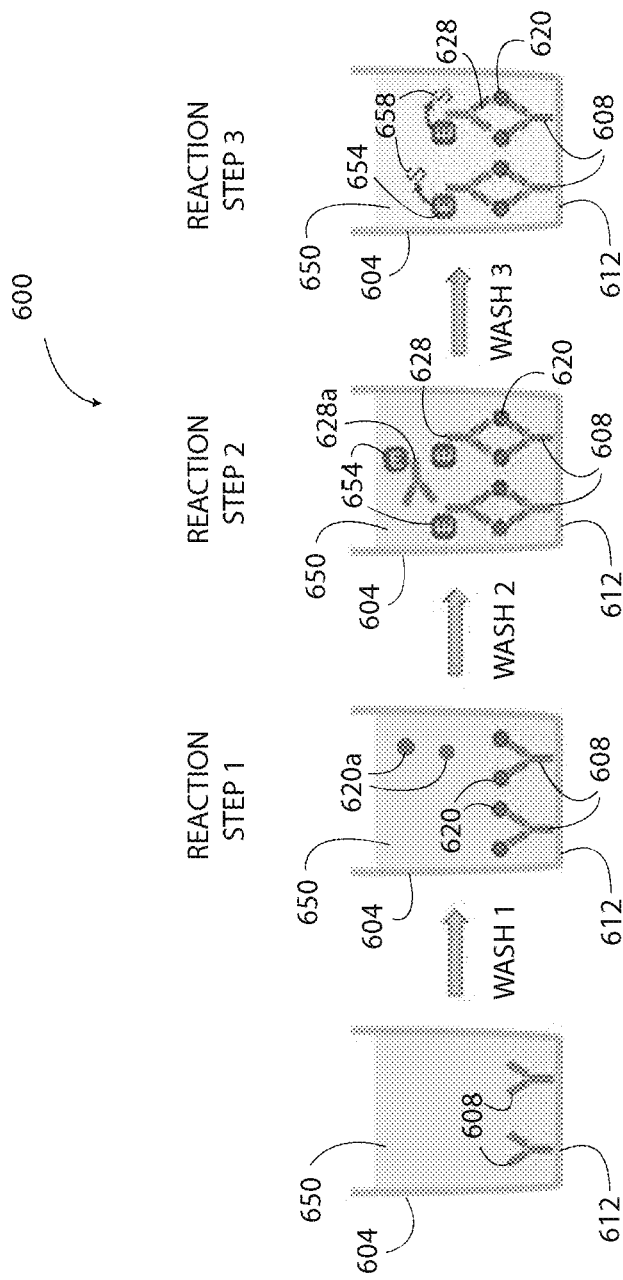
FIG. 13 is a prior art block diagram illustrating multiple washing steps and multiple reaction steps of a conventional ELISA system.

The systems 100, 400, 500 disclosed herein offer numerous advantages over prior art ELISA systems. As shown by comparing FIGS. 12 and 13, the systems 100, 400, 500 disclosed herein have only one wash step and only one reaction step prior to detecting the detected values. In particular, as shown in FIG. 12, the wash (i.e. wash 1) occurs after the capture agent 166 is bound to the electrode 140 and prior to adding the target substance 158 to the well 188. No further washing steps or reaction steps are utilized; thus, the systems 100, 400, 500 are a single-step ELISA. Whereas, as shown in FIG. 13, a conventional ELISA system 600 has at least three washes and at least three reaction steps prior to detecting the output. The conventional ELISA system 600 includes a well 604 that does not include electrodes. The capture agent 608 is bound directly to the bottom surface 612 of the well 604. Conventional ELISA has a first wash (i.e. wash 1) after the capture agent 608 is bound to the well 604 and the surface 612. Next, a second wash (i.e. wash 2) is performed after adding the target substance 620 to the well 604 to remove the molecules of unbound target substance 620a that have not bound to the capture agent 608. A third wash (i.e. wash 3) is performed after adding the detection agent 628 to the well 604 to remove the molecules of unbound detection agent 628a that have not bound to the target substance 620. After the third wash, a temporally controlled enzymatic development reaction provides an output value.

The well 604 provides an output value by exhibiting a change in color of the reagent solution 650 that is detectable with either test equipment (not shown) or by visual observation from the technician. Specifically, the detection agent 628 is labeled with an enzyme 654 that is configured to react with substrates 658 in the reagent solution 650 to generate products that change the color of the reagent solution 650 or to form visible local precipitates on surface 612. The system 600 does not use a change in pH to detect the target substance 620.

The systems 100, 400, 500 and method 300 disclosed herein are much less prone to user error than the conventional ELISA system 600 and, therefore, provide more reproducible and more reliable test results. With each wash step in the ELISA process, there exists the possibility that the technician will disrupt the test process. For example, in the conventional ELISA system 600 if the well 604 is washed to remove the unbound molecules 620a of the test substance 620, then it is possible to disturb and to remove some of the bound molecules of the test substance 620, thereby affecting the test results by reducing the quantity of the test substance 620 that is bound to the capture agent 608. Thus, it is typically desirable to reduce the number of washes. Moreover, each wash takes a certain amount of time; thus, high-throughput is another advantage of the systems 100, 400, 500. Having an hour-long reaction for each component (capture agent 608, target substance 620, and detection agent 628) and at least three to five washing steps of at least five minutes each dramatically increases the reaction time of the conventional ELISA system 600 as compared to the single-step ELISA method 300, as disclosed herein. Since the systems 100, 400, 500 use fewer washes, the systems 100, 400, 500 generate test results more quickly and with more reliability than the conventional ELISA system 600 of FIG. 13, thereby making the systems 100, 400, 500 particularly well-suited for point-of-care systems. If a multiplexing format is adopted (i.e. as shown in FIGS. 8 and 9), the throughput of the system 400, 500 is increased even more as compared to the conventional ELISA system 600.

As shown in FIGS. 14A, 14B, 15, and 16, an ELISA system 700 utilizes pH modulation and a FRET-based detection method. FRET (fluorescence resonance energy transfer)-based detection methods use a pair of fluorophores to detect the target substance 158. When one fluorophore (donor) of the pair gets excited with a light at the right excitation wave length, the energy transfers to the excited level of the other fluorophore and the other fluorophore (acceptor) emits a fluorescence signal at a corresponding emission wave length. Depending on the FRET pair used, the energy transfer could also induce a quenching of a light signal instead of the emission of the light signal or the release of the fluorescence signal.

Figure 15:
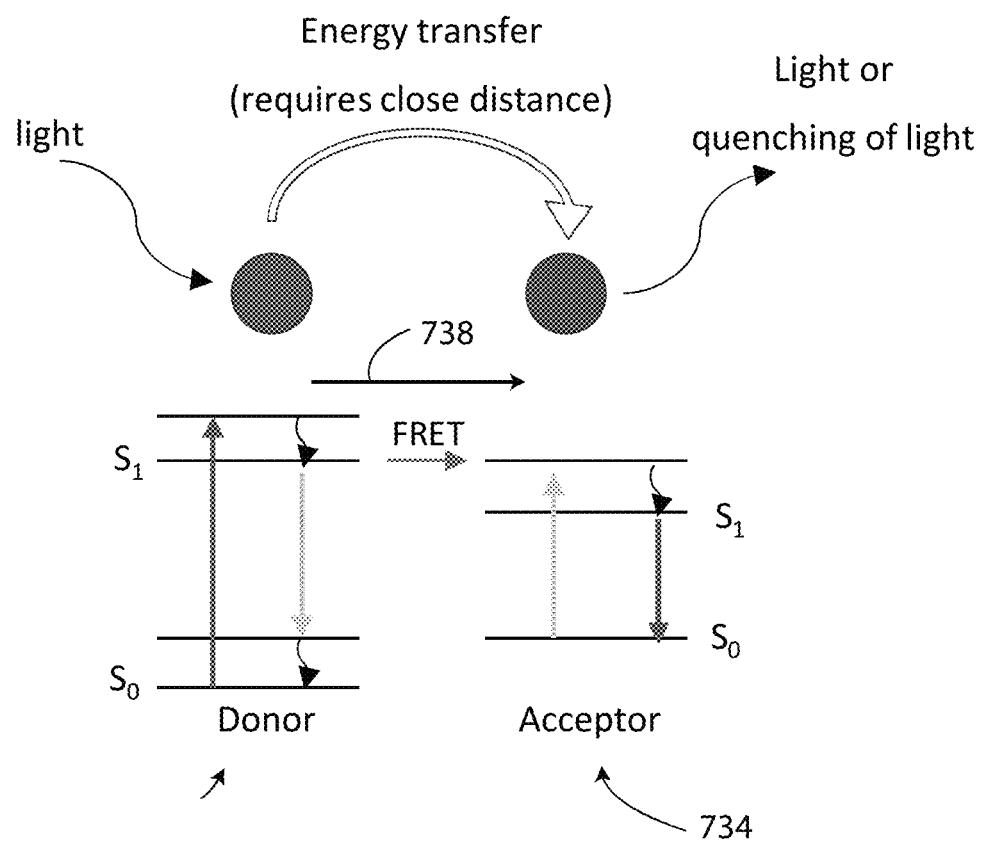
FIG. 15 is a block diagram illustrating FRET as used by the system of FIG. 14A.

As set forth below, FRET-based detection systems, such as the system 700, reduce the number of false-detection molecules (such as false-detection molecules 212, FIG. 1). To this end, the system 700 uses capture agents and detection agents labeled with a FRET pair: a capture agent labeled with a donor molecule and a detection agent labeled with an acceptor molecule or vice versa. At least one of the donor or the acceptor generates a pH-dependent output signal (such as a light output). As shown in FIG. 15, the output signal is generated only when the donor and the acceptor are located within a predetermined distance 738 from each other, through the binding to the same target substance 158, and the pH is modulated to the desired predetermined pH. Another benefit is that FRET systems 700 can quench as well as excite the fluorescence, as a result, the presence of the target substance(s) 158 can be indicated as either an output signal including a fluorescence signal (emission of light) or as an output signal including an absence of light (a quenched signal). Exemplary FRET pairs (i.e. donor and acceptor pairs) are described in FIG. 16 and include fluorescein isothiocyanate (FITC) and an isothiocyanate derivate of tetramethylrhodamine (TRITC), FAM and TRITC, and Oregon Green 488 and tetramethylrhodamine (TMR). FIG. 16 also sets forth the excitation and emission wavelengths of each donor and acceptor pair, as well as which of the pairs is pH-sensitive.

Figure 14A:
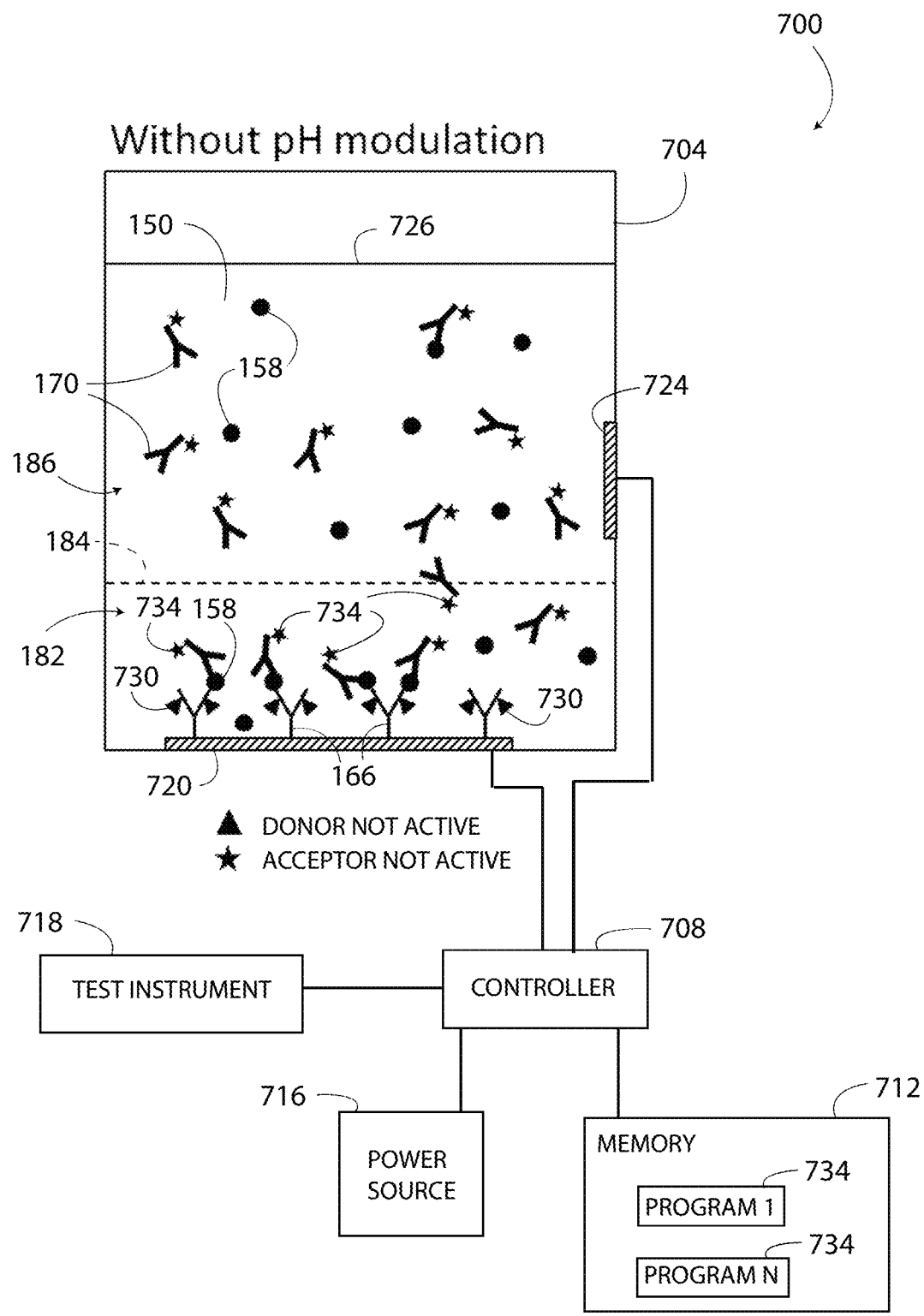
FIG. 14A is a block diagram illustrating a FRET-based single-step ELISA system, as disclosed herein, prior to modulating the pH of a modulation zone.
Figure 14B:
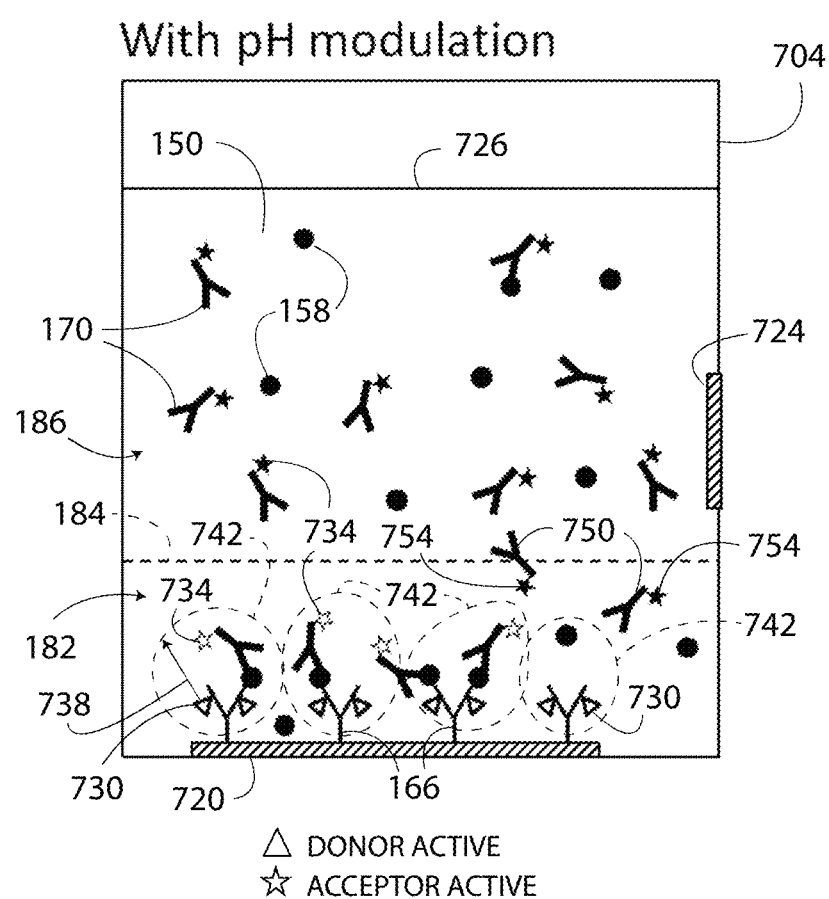
FIG. 14B is a block diagram of a portion of the FRET-based system of FIG. 14A shown during pH modulation of the modulation zone.

An exemplary FRET-based system 700 is shown in FIGS. 14A and 14B. The system 700 is configured to detect the presence and/or concentration of a target substance 158 without requiring a separate control well. The system 700 includes a well 704, a controller 708, a memory 712, a power source 716, and a test instrument 718. The well 704 includes electrodes 720, 724 and a test sample 726 located therein. The electrodes 720, 724, the memory 712, the power source 716, and the test instrument 718 are each electrically connected to the controller 708. The memory 712 includes programs 734 configured to cause the controller 708 to implement a method similar/the same as the method 300 of FIG. 3. The controller 708 is substantially the same as the controller 132, the power source 716 is substantially the same as the power source 116, and the memory 712 is substantially the same as the memory 124.

The system 700 includes a capture agent 166 bound to the electrode 720 and the test sample 726 includes the target substance 158 and a detection agent 170. In this example, the capture agent 166 and the detection agent 170 include a FRET pair. Specifically, the capture agent 166 is label with a donor molecule 730 and the detection agent 170 is labeled with an acceptor molecule 734. In other embodiments, the capture agent 166 is labeled with the acceptor molecule 734 and the detection agent 170 is labeled with the donor molecule 730. In FIG. 14A, the reagent solution 150 is not being pH modulated. Accordingly, the pH of the test sample 726 is substantially uniform throughout and neither the donor molecule 730 nor the acceptor molecule 734 is active.

In one embodiment, the acceptor molecule 734 is different from the tag 174 in that the acceptor molecule 734 does not generate an output signal or undergo a change directly in response to the localized change in pH of the reagent solution 150. Instead, the acceptor molecule 734 undergoes the change only when located within the predetermined distance 738 (FIG. 14B) from an activated donor molecule 730. The donor molecule 730 undergoes a change (i.e. a first change) in response to the localized change in pH of the reagent solution 150, but the change undergone by the donor molecule 730 is not detectable by the test instrument 718. Instead, the donor molecule 730 activates the acceptor molecules 734 located within the predetermined distance 738 therefrom or within a predetermined donor region 742. When the controller 708 modulates the pH of the modulation zone 182, only the acceptor molecules 734 located within the predetermine distance 738 from the activated donor molecules 730 generate the output signal (i.e. a second change) detectable by the test instrument 718. The non-modulation zone 186 is located above the modulation zone 182.

In operation, as shown in FIG. 14B, the system 700 is operable to detect the presence and/or the concentration of the target substance 158 in the test sample 726. To begin, the system 700 locally modulates the pH in the modulation zone 182 below the modulation line 184. The modulated pH activates the donor molecules 730 of the capture agent 166 and causes only the acceptor molecules 734 located within the donor regions 742 to undergo a change and to generate an output signal that is detectable by the test instrument 718. As shown in FIG. 14B, two nearby detection agents 750 have acceptor molecules 754 located below the modulation line 184 in the modulation zone 182. The acceptor molecules 754 are spaced outside of the donor regions 742 and are not activated and do not contribute to the output signal that is detectable by the test instrument 718.

The change undergone by the acceptor molecules 734 located inside of the donor regions 742 is the output signal of the system 700. In one embodiment, no control signal is generated by the system 700 and no control signal is subtracted from the output signal because the system 700 eliminates "false positives" using the FRET concept. In short, using FRET causes only those acceptor molecules 734 most likely to be bound to the target substance 158 to generate an output. FRET improves the reliability of the test by simply preventing the acceptor molecules 734 that are not bound to the target substance 158 but are located below the modulation line 184 from contributing to the output signal. In another embodiment, a control signal is obtained from the system 700 to compensate for any fluorescent output of the acceptor molecules 734 that is not on account of the pH modulation. This fluorescent output is referred to herein as a background level of florescent output. The background level of fluorescence output, if any, is subtracted from the output signal generated by pH-modulated tags 734.

Based on the above, in the FRET-based system 700, at least one of the donor molecule 730 and the acceptor molecule 734 is pH-sensitive. Specifically, in a first configuration of the FRET-based system 700, the donor molecule 730 is pH-sensitive and the acceptor molecule 734 is not pH-sensitive. In a second configuration of the FRET-based system 700, the donor molecule 730 is not pH-sensitive and the acceptor molecule 734 is pH-sensitive. In a third configuration of the FRET-based system 700, both the donor molecule 730 and the acceptor molecule 734 are pH-sensitive.

In a further configuration of the FRET-based system 700, pH modulation is not required in order to detect the presence and/or the concentration of the target substance 158 in the sample 726. In such an embodiment, neither of the donor molecules 730 and the acceptor molecules 734 is pH-sensitive, and the single-step ELISA is performed without modulating the pH of the reagent 150. Specifically, the donor molecules 730 and the acceptor molecules 734 are select to have a detectable output (either light emission or a quenched signal) when located less than the predetermined distance 738 from each other. Since, the donor molecules 730 are bound to the electrode 720 the detectable output is mostly influenced by the acceptor molecules 734 of the molecules of the detection agent 170 that are bound to the target substance 158. The molecules of unbound detection agent 170 are typically located further than the predetermined distance 738 from the donor molecules 730 and, therefore, do not contribute to the detectable output. The pH modulation approach described herein typically provides an increased level of accuracy as compared to a FRET-based system that does not use pH modulation.

Figure 17:
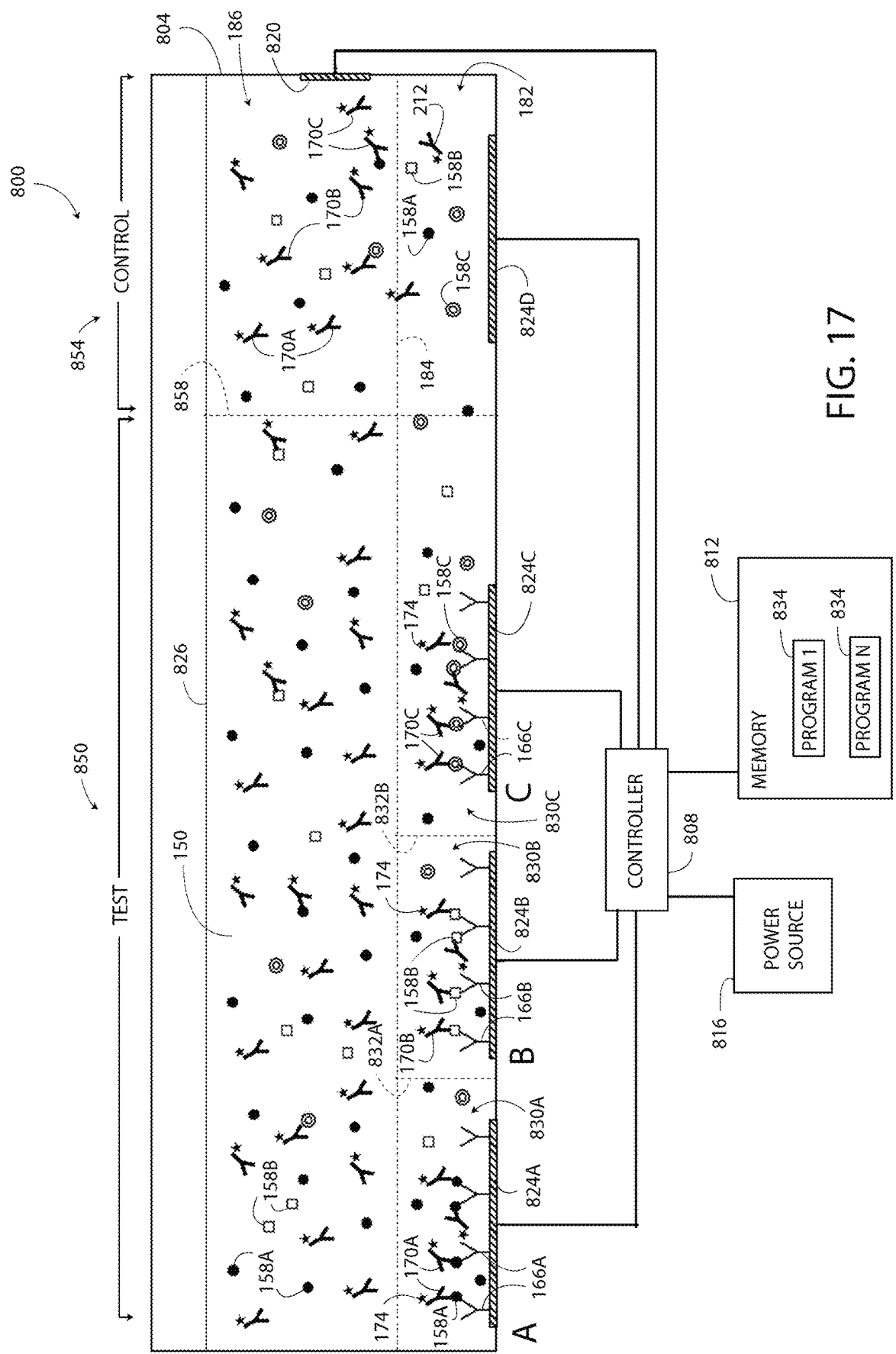
FIG. 17 is a block diagram illustrating another exemplary multiplexed embodiment of a single-step ELISA system, as disclosed herein.

Another multiplexed system 800 is shown in FIG. 17. The system 800 is configured to detect the presence and/or concentration of multiple/different types of target substances 158A, 158B, 158C within a sample 826 using a single well 804 without a separate control well. The system 800 includes the well 804, a controller 808, a memory 812, and a power source 816. The system 800 may also include a test instrument (not shown), such as the test instrument 518 of FIG. 9. The well 804 includes a common electrode 820 shared by test electrodes 824A, 824B, 824C and a control electrode 824D. The electrodes 824A, 824B, 824C, 824D, 820, the memory 812, and the power source 816 are each electrically connected to the controller 808. The memory 812 includes programs 834 configured to cause the controller 808 to implement a method similar/the same as the method 300 of FIG. 3. The controller 808 is substantially the same as the controller 132, the power source 816 is substantially the same as the power source 116, and the memory 812 is substantially the same as the memory 124.

The system 800 of FIG. 17 is similar to the system 500 of FIG. 9, but differs in that the well 804 is a combination of the test well 504 and the control well 506 of the system 500. The well 804 includes a sample 826 having three different target substances 158A, 158B, 158C and three different detection agents 170A, 170B, 170C within the reagent solution 150 that include tags 174. Moreover, there are three different capture agents 166A, 166B, 166C bound to the corresponding electrodes 824A, 824B, 824C. The target substances 158A, 158B, 158C are each illustrated differently in FIG. 17. The capture agents 166A, 166B, 166C and the detection agents 170A, 170B, 170C are distinguishable by reference numeral and letter in FIG. 17, but have the same graphical depiction. The capture agent 166A is bound to only the electrode 824A, the capture agent 166B is bound to only the electrode 824B, and the capture agent 166C is bound to only the electrode 824C. The system 800 includes substantially rectangular (in cross-section) sub-modulation zones 830A, 830B, 830C. Line 832A identifies a boundary between sub-modulation zone 830A and sub-modulation zone 830B and line 832B identifies a boundary between sub-modulation zone 830B and sub-modulation zone 820C. The modulation line 184 separates the modulation zone 182 from the non-modulation zone 186.

The well 804 includes a test region 850 and a control region 854. A boundary line 858 identifies a boundary between the regions 850, 854, but no physical barrier is present between the regions 850, 854. That is, the regions 850, 854 are fluidically connected and the sample 826 moves freely between the two regions 850, 854. The control electrode 824D does not include any molecules of the capture agent (including the capture agents 166A, 166B, 166C) attached thereto. Stated differently, the control electrode 824D is void of a capture agent 166A, 166B, 166C. Accordingly, even though the control electrode 824D is exposed to the sample 826 that includes the target substances 158A, 158B, 158C, there is no specific binding between the control electrode 824D and any molecules of the sample 826. That is, none of the molecules within the sample 826 are configured to bind directly to the control electrode 824D. Therefore, an output signal (i.e. a light output or other detectable output) of the control region 854 is based on only the false detection molecules 212. In operation, the output signal of the control region 854 is subtracted from the output signals (i.e. a light output or other detectable output) of the sub-modulation zones 830A, 830B, 830C to arrive at the results of the assay.

The system 800 enables an assay to be performed in a single-well format either for a sample having single target substance or the multiplexed sample 826 having multiple target substances 158A, 158B, 158C. The system 800 is illustrated in FIG. 17 in a format for use with the multiplexed sample 826.

Figure 18:
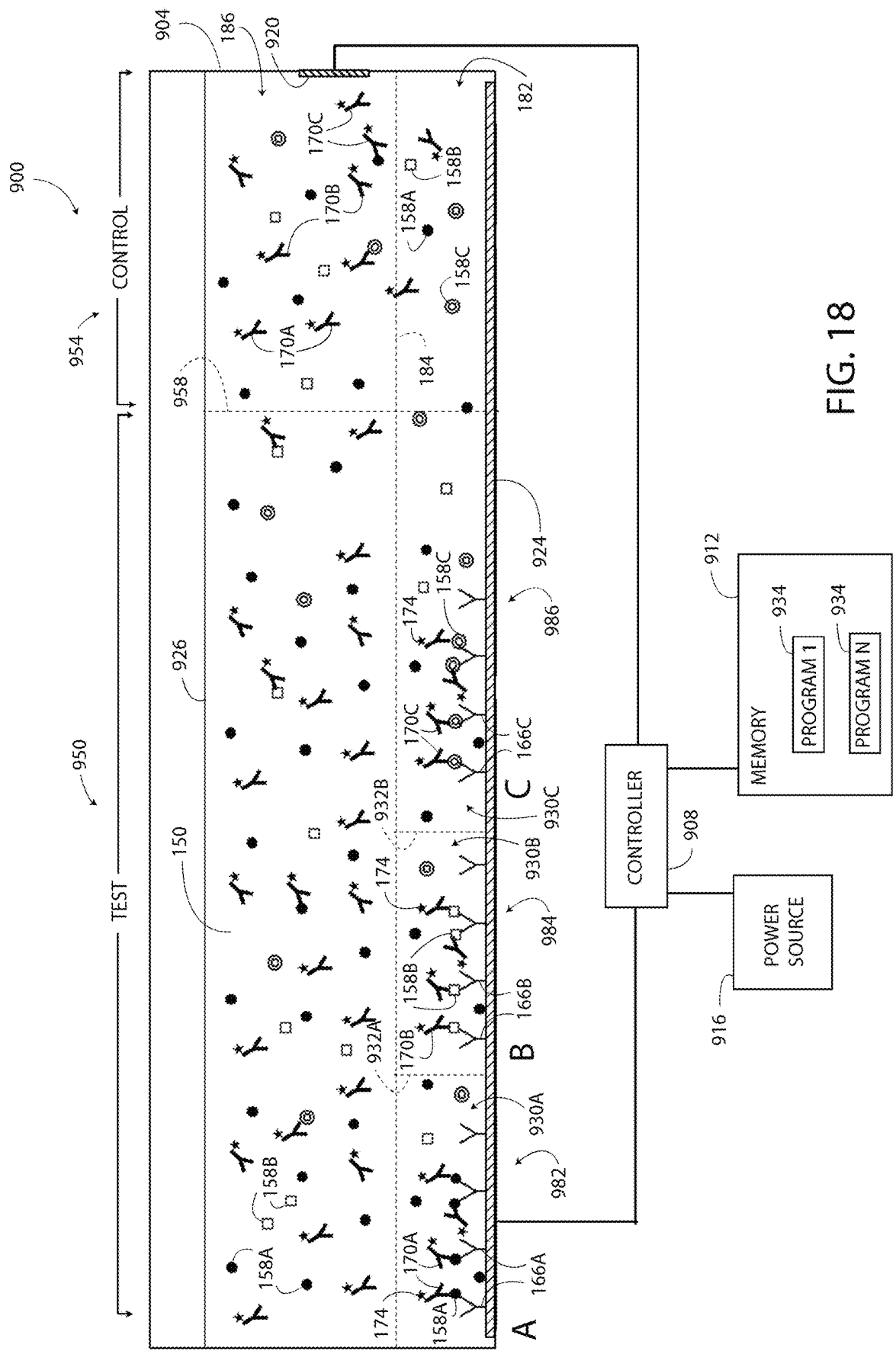
FIG. 18 is a block diagram illustrating yet another exemplary multiplexed embodiment of a single-step ELISA system, as disclosed herein.

A further multiplexed system 900 is shown in FIG. 18. The system 900 is configured to detect the presence and/or concentration of multiple/different types of target substances 158A, 158B, 158C within a sample 926 using a single well 904 without a separate control well. The system 900 includes the well 904, a controller 908, a memory 912, and a power source 916. The system 900 may also include a test instrument (not shown), such as the test instrument 518 of FIG. 9. The well 904 includes a common electrode 920 and a common test electrode 924. The electrodes 920, 924, the memory 912, and the power source 916 are each electrically connected to the controller 908. The memory 912 includes programs 934 configured to cause the controller 908 to implement a method similar/the same as the method 300 of FIG. 3. The controller 908 is substantially the same as the controller 132, the power source 916 is substantially the same as the power source 116, and the memory 912 is substantially the same as the memory 124.

The system 900 of FIG. 18 is substantially the same as the system 800 of FIG. 17, but differs in that the system 900 includes only one test electrode 920 instead of the spaced apart multiple test electrodes 824A, 824B, 824C of FIG. 17. As shown in FIG. 18, the single electrode 920 extends from the test region 950 to the control region 954. Moreover, three different types of the capture agent 166A, 166B, 166C are bound to the electrode 920 at three different patterned sites 982, 984, 986 of the electrode 920. The patterned sites 982, 984, 986 may each have the same pattern or the sites 982, 984, 986 may each have a different pattern that corresponds to a particular one of the capture agents 166A, 166B, 166C. That is, for example, the patterned site 982 may be patterned in a manner that causes only the capture agent 166A to bind thereto while preventing the capture agents 166B, 166C from binding thereto. The electrode 924 may be patterned using a spotted array approach, in one embodiment.

The sample 926 includes three different target substances 158A, 158B, 158C and three different detection agents 170A, 170B, 170C within the reagent solution 150 that include tags 174. Moreover, the three different capture agents 166A, 166B, 166C are bound to the electrode 924. The target substances 158A, 158B, 158C are each illustrated differently in FIG. 18. The capture agents 166A, 166B, 166C and the detection agents 170A, 170B, 170C are distinguishable by reference numeral and letter in FIG. 18, but have the same graphical depiction. The capture agent 166A is bound to only the patterned site 982, the capture agent 166B is bound to only the patterned site 984, and the capture agent 166C is bound to only the patterned site 986. There are no bound capture agent molecules 166A, 166B, 166C located in the control region 954. The system 900 includes substantially rectangular (in cross-section) sub-modulation zones 930A, 930B, 930C. Line 932A identifies a boundary between sub-modulation zone 930A and sub-modulation zone 930B, and line 932B identifies a boundary between sub-modulation zone 930B and sub-modulation zone 920C. The modulation line 184 separates the modulation zone 182 from the non-modulation zone 186. A boundary line 958 identifies a boundary between the regions 950, 954, but no physical barrier is present between the regions 950, 954. That is, the regions 950, 954 are fluidically connected and the sample 926 moves freely between the two regions 950, 954.

In detecting the output of the system 900, the test instrument (such as the test instrument 518) is positioned to detect the light output from the sub-modulation zone 930A using the sensor 522A, to detect the light output from the sub-modulation zone 930B using the sensor 522B, and to detect the light output from the sub-modulation zone 930C using the sensor 522C. The control signal is detected by another sensor of the test instrument 518 in any portion of the control region 954.

While the disclosure has been illustrated and described in detail in the drawings and foregoing description, the same should be considered as illustrative and not restrictive in character. It is understood that only the preferred embodiments have been presented and that all changes, modifications, and further applications that come within the spirit of the disclosure are desired to be protected.

What is claimed is:

1. A method for detecting a presence and/or a concentration of a target substance in a reagent solution using enzyme-linked immunosorbent assay (ELISA) comprising:
    binding the target substance directly or indirectly to an electrode;
    binding a detection agent directly or indirectly to the bound target substance;
    modulating a pH of only a portion of the reagent solution in which the bound detection agent is located using the electrode, the modulated pH of the portion of the reagent solution causing the bound detection agent to undergo a change; and
    detecting the change in the bound detection agent, the detected change corresponding to the presence of the target substance in the reagent solution and/or the concentration of the target substance in the reagent solution.

2. The method of claim 1, further comprising:
binding a capture agent to the electrode; and
binding the target substance directly or indirectly to the capture agent.

3. The method of claim 1, wherein the detection agent includes a pH-sensitive reporter, the method further comprising:
energizing the electrode with a direct current electrical signal for a predetermined time period to modulate the pH of only the portion of the reagent solution from a first value to a second value, the second value different from the first value,
wherein the pH-sensitive reporter undergoes the change in response to the portion of the reagent solution having the second value of pH.

4. The method of claim 1, wherein the portion of the reagent solution is a first portion of the reagent solution and the first portion of the reagent solution is located in a modulation zone, the method further comprising:
preventing modulation of a pH of a second portion of the reagent solution, the second portion of the reagent solution located in a non-modulation zone,
wherein unbound molecules of the detection agent are located in the non-modulation zone, and
wherein the unbound molecules of the detection agent do not undergo the change.

5. The method of claim 1, further comprising:
binding a capture agent to an occupied area including an area of the electrode;
blocking an unoccupied area adjacent to the occupied area to prevent binding of the capture agent to the unoccupied area;
removing unbound capture agent from the occupied area and the unoccupied area in a washing step;
binding the target substance directly or indirectly to the bound capture agent; and
detecting the change in the bound detection agent without any further washing steps.

6. The method of claim 1, wherein the detection agent includes a pH-sensitive reporter, the method further comprising:
detecting the change in the bound detection agent as an intensity of light emitted by the pH-sensitive reporter.

7. A method for detecting a target substance using enzyme-linked immunosorbent assay (ELISA) comprising:
binding the target substance directly or indirectly to a first electrode located in a test well including a reagent solution;
adding a detection agent to the test well, a bound portion of the detection agent bound directly or indirectly to the bound target substance and an unbound portion of the detection agent unbound to the bound target substance;

adding additional detection agent to a control well that includes additional reagent solution and that does not include the target substance, a second electrode located in the control well;
modulating a pH of only a portion of the reagent solution in the test well in which the bound portion of the detection agent is located to cause the bound portion of the detection agent located in the portion of the reagent solution and the unbound portion of the detection agent located in the portion of the reagent solution to undergo a first change using the first electrode;
modulating a pH of only a corresponding portion of the additional reagent solution located in the control well to cause a corresponding portion of the additional detection agent located in the corresponding portion of the additional reagent solution to undergo a second change using the second electrode; and
detecting the first change as a first detected value;
detecting the second change as a second detected value; and
generating a test value as a comparison of the first detected value to the second detected value, the generated test value corresponding to a presence of the target substance in the test well and/or a concentration of the target substance in the test well.

8. The method of claim 7, further comprising:
detecting the first detected value as a value representing a sum of the bound portion of the detection agent located in the portion of the reagent solution having the modulated pH and the unbound portion of the detection agent located in the portion of the reagent solution having the modulated pH; and
detecting the second detected value as a value representing unbound detection agent located in the portion of the other reagent solution having a modulated pH.

9. The method of claim 8, further comprising:
subtracting the second detected value from the first detected value to generate the test value to isolate an output of the bound detection agent located in the portion of the reagent solution having the modulated pH.

10. The method of claim 7, further comprising:
adding the reagent solution and the other reagent solution to the same space; and
maintaining a physical separation between the reagent solution and the other reagent solution.

11. The method of claim 7, wherein the detection agent and the other detection agent each include a pH-sensitive reporter and the method further comprises:
detecting the first change as an intensity of light emitted by the pH-sensitive reporter of the bound detection agent; and
detecting the second change as another intensity of light emitted by the pH-sensitive reporter of the other detection agent located in the corresponding portion of the additional reagent solution.

* * * * *